US007417180B2

(12) United States Patent
Ashikari et al.

(10) Patent No.: US 7,417,180 B2
(45) Date of Patent: Aug. 26, 2008

(54) GENES FOR INCREASING GRAIN YIELD AND USES THEREOF

(75) Inventors: Motoyuki Ashikari, Nagoya (JP); Makoto Matsuoka, Nagoya (JP); Shaoyang Lin, Wako (JP); Toshio Yamamoto, Wako (JP); Asuka Nishimura, Wako (JP); Tomonori Takashi, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 10/534,593

(22) PCT Filed: Nov. 13, 2003

(86) PCT No.: PCT/JP03/14434

§ 371 (c)(1),
(2), (4) Date: Oct. 31, 2005

(87) PCT Pub. No.: WO2004/044200

PCT Pub. Date: May 27, 2004

(65) Prior Publication Data

US 2006/0123507 A1 Jun. 8, 2006

Related U.S. Application Data

(60) Provisional application No. 60/425,919, filed on Nov. 13, 2002.

(51) Int. Cl.
*A01H 1/00* (2006.01)
*C07H 21/02* (2006.01)
*C07H 21/04* (2006.01)
*C07K 14/415* (2006.01)
*C12N 15/29* (2006.01)

(52) U.S. Cl. .......................... 800/295; 435/6; 435/468; 435/419; 435/320.1; 530/370; 536/23.2; 536/24.3; 800/278

(58) Field of Classification Search ...................... 435/6, 435/468, 183, 419, 320.1; 530/370; 536/23.2, 536/24.3, 24.33; 800/278, 295
See application file for complete search history.

(56) References Cited

U.S. PATENT DOCUMENTS 6,229,066 B1 * 5/2001 Morris .......................... 800/279
2007/0020621 A1 * 1/2007 Boukharov et al. ............. 435/6

FOREIGN PATENT DOCUMENTS

| WO | WO 99/06571 A1 | 2/1999 |
| WO | WO-00/63401 A1 | 10/2000 |
| WO | WO-01/96580 A2 | 12/2001 |
| WO | WO 03/000898 A1 | 1/2003 |
| WO | WO 03000898 A1 * | 1/2003 |
| WO | WO-03/050287 A2 | 6/2003 |

OTHER PUBLICATIONS

EMBL-EBI, Accession No. AP003200, "Oryza sativa (japonica cultivar-group) genomic DNA, chromosome 1, BAC clone:B1046G12," dated Feb. 22, 2001.
EMBL-EBI, Accession No. AP003244, "Oryza sative (japonica cultivar-group) genomic DNA, chromosone 1, PAC clone:P0419B01," dated Feb. 22, 2001.
Jones, Robert J., et al., "Role and function of cytokinin oxidase in plants," *Plant Growth Regulation*, vol. 23:123-134 (1997).
Schmülling, Thomas, "New Insights into the Functions of Cytokinins in Plant Development," *J. Plant Growth*, vol. 21:40-49 (2002).
Werner, Tomáš, et al., "Regulation of plant growth by cytokinin," *PNAS*, vol. 98(18):10487-10492 (2001).
European Search Report Application No. 03811127.4-2405, dated Jan. 16, 2006.
Galuszka, Petr et al, "Cytokinin oxidase or dehydrogenase? Mechanism of cytokinin degradation in cereals," *Eur. J. Biochem.*, vol. 268:450-461 (2001).
Morris, Roy O. et al, "Isolation of a Gene Encoding a Glycosylated Cytokinin Oxidase from Maize," *Biochemical and Biophysical Research Communicatons*, vol. 255:328-333 (1999).
Ashikari, M. et al. "Cytokinin Oxidase Regulates Rice Grain Production" *ScienceExpress* (Jun. 23, 2005), vol. 10, No. 1126, pp. 1-8.
Bilyeu, K.D. et al. "Dynamics of expression and distribution of cytokinin oxidase/dehydrogenase in developing maize kernels." *Plant Growth Regulation* (Mar. 2003), vol. 39, No. 3, pp. 195-203.
Houba-Herin, N. et al. "Cytokinin oxidase from Zea mays: purification, cDNA cloning and expression in moss protoplasts." *Plant J.* (1999), vol. 17, No. 6, pp. 615-626.
Joseph, T. et al. "Changes in cytokinins and cytokinin oxidase activity in developing maize kernels and the effects of exogenous cytokinin on kernel development." *Plant Physiol. Biochem.* (1995), vol. 33, No. 3, pp. 327-336.
Sasaki, T. et al. "The genome sequence and structure of rice chromosome 1." *Nature* (Nov. 2002), vol. 420, No. 6913, pp. 312-316.
Yang, S.H. et al. "Functional characterization of a cytokinin oxidase gene DSCKX1 in Dendrobium orchid." *Plant Mol. Biol.* (Jan. 2003), vol. 51, No. 2, pp. 237-248.
Watanabe, Katsuji et al., "2-Phenyl-5*H*-pyrazolo[5,1-α]isoquinolin-5-ones: Development of New Auxin Transport Inhibitors and Their Plant Growth Regulating Properties," *J. Agric. Food Chem.*, vol. 42:2311-2316 (1994).

* cited by examiner

*Primary Examiner*—Phuong T Bui
(74) *Attorney, Agent, or Firm*—Lahive & Cockfield, LLP; Elizabeth A Hanley, Esq.; Jeanne M DiGiorgio, Esq.

(57) ABSTRACT

A gene that regulates the increase and decrease of the particle-bearing number (including glumous flowers, fruits, and seeds) of plants was successfully isolated and identified by a linkage analysis. In addition, breeding methods that utilize this gene to increase the particle-bearing number (including glumous flowers, fruits, and seeds) of plants were also discovered. The present invention is useful in fields such as breeding of improved plant varieties.

11 Claims, 10 Drawing Sheets

SEQUENCE LISTING

```
<160> NUMBER OF SEQ ID NOS: 14

<210> SEQ ID NO 1
<211> LENGTH: 5400
<212> TYPE: DNA
<213> ORGANISM: Oryza sativa
<220> FEATURE:
<221> NAME/KEY: CDS
<222> LOCATION: (172)..(816)
<220> FEATURE:
<221> NAME/KEY: CDS
<222> LOCATION: (908)..(1375)
<220> FEATURE:
<221> NAME/KEY: CDS
<222> LOCATION: (3824)..(4090)
<220> FEATURE:
<221> NAME/KEY: CDS
<222> LOCATION: (4542)..(4856)
<220> FEATURE:
<221> NAME/KEY: Intron
<222> LOCATION: (1)..(108)
```

-continued

```
<220> FEATURE:
<221> NAME/KEY: Exon
<222> LOCATION: (109)..(817)
<220> FEATURE:
<221> NAME/KEY: Intron
<222> LOCATION: (818)..(908)
<220> FEATURE:
<221> NAME/KEY: Exon
<222> LOCATION: (909)..(1375)
<220> FEATURE:
<221> NAME/KEY: Intron
<222> LOCATION: (1376)..(3823)
<220> FEATURE:
<221> NAME/KEY: Exon
<222> LOCATION: (3824)..(4089)
<220> FEATURE:
<221> NAME/KEY: Intron
<222> LOCATION: (4090)..(4540)
<220> FEATURE:
<221> NAME/KEY: Exon
<222> LOCATION: (4541)..(5400)

<400> SEQUENCE: 1
```

| | |
|---|---:|
| acagctctac tgtctatcta gctatctatc agctgccttc catcgtcagc acacaaacta | 60 |
| cacaagaatc tgcttattta taggccacct tgtcccttct acaatggtgc aagaacacac | 120 |
| aaattcacac acacactgac acacacaaac cgatcgattg attgattgat a atg aag | 177 |
|                                                                                                                            Met Lys | |
|                                                                                                                             1 | |
| caa gag cag gtc agg atg gca gtg ctc ctc atg ctc aac tgc ttc gtc | 225 |
| Gln Glu Gln Val Arg Met Ala Val Leu Leu Met Leu Asn Cys Phe Val | |
|      5                       10                     15 | |
| aag gcc acg gcg ccg ccg cca tgg ccg ccg tcg gct tcg tcc gcc tcc | 273 |
| Lys Ala Thr Ala Pro Pro Pro Trp Pro Pro Ser Ala Ser Ser Ala Ser | |
|  20                       25                   30 | |
| ttc ctc gac gac ctc ggc gac ctc ggc atc gcg ccg ctc atc cgc gcc | 321 |
| Phe Leu Asp Asp Leu Gly Asp Leu Gly Ile Ala Pro Leu Ile Arg Ala | |
| 35                 40                   45                   50 | |
| gac gag gcg ggc acc gcg cgc gcc tcc gcc gac ttt ggc aac ctc tcc | 369 |
| Asp Glu Ala Gly Thr Ala Arg Ala Ser Ala Asp Phe Gly Asn Leu Ser | |
|                     55                     60                   65 | |
| gtc gcc ggc gtc ggg gcg cct cgg ctc gcc gcc gcc gcc gtg ctc | 417 |
| Val Ala Gly Val Gly Ala Pro Arg Leu Ala Ala Ala Ala Val Leu | |
|          70                   75                   80 | |
| tac ccg tcg cgc ccc gcc gac atc gcc gcg ctg ctg cgc gcg tcg tgc | 465 |
| Tyr Pro Ser Arg Pro Ala Asp Ile Ala Ala Leu Leu Arg Ala Ser Cys | |
|         85                   90                   95 | |
| gca cgc ccg gcg ccg ttc gcg gtg tcc gcg cgg ggg tgt ggc cac tcg | 513 |
| Ala Arg Pro Ala Pro Phe Ala Val Ser Ala Arg Gly Cys Gly His Ser | |
| 100                 105                  110 | |
| gtg cac ggc cag gcc tcc gcg ccc gac ggc gtc gtc gac atg gcg | 561 |
| Val His Gly Gln Ala Ser Ala Pro Asp Gly Val Val Asp Met Ala | |
| 115                 120                 125               130 | |
| tcg ctc ggc cgc ctg cag ggc ggc ggc gcg cgg cgc ctc gcc gtg tca | 609 |
| Ser Leu Gly Arg Leu Gln Gly Gly Gly Ala Arg Arg Leu Ala Val Ser | |
|                     135                  140                  145 | |
| gtg gag ggg cgg tac gtc gac gcc ggc ggc gag cag ctg tgg gtg gac | 657 |
| Val Glu Gly Arg Tyr Val Asp Ala Gly Gly Glu Gln Leu Trp Val Asp | |
|                 150                  155                  160 | |
| gtg ctg cgc gcg tcc atg gcg cac ggg ctc acg ccg gtg tcg tgg aca | 705 |
| Val Leu Arg Ala Ser Met Ala His Gly Leu Thr Pro Val Ser Trp Thr | |
|              165                  170                  175 | |
| gac tac ctc cac ctc acc gtc ggc ggc acg ctg tcc aac gcc ggc atc | 753 |
| Asp Tyr Leu His Leu Thr Val Gly Gly Thr Leu Ser Asn Ala Gly Ile | |
|          180                  185                  190 | |

```
agc ggc cag gcc ttc cgc cat ggc ccc cag att tcc aac gtg cta gag      801
Ser Gly Gln Ala Phe Arg His Gly Pro Gln Ile Ser Asn Val Leu Glu
195                 200                 205                 210 ctc gac gtc atc acc ggtacgtaga tccatcacat ctactaagac acgcgccgcc      856
Leu Asp Val Ile Thr
                215 atgatcgagg taattaaggt ataggtgttt tgacgtatac atgtatctgc a ggt gtc     913
                                                        Gly Val ggg gag atg gtg acg tgc tcg aag gag aag gcg ccg gac ctg ttc gac      961
Gly Glu Met Val Thr Cys Ser Lys Glu Lys Ala Pro Asp Leu Phe Asp
            220                 225                 230 gcg gtg ctg ggc ggg ctg ggc cag ttc ggc gtc atc acg cgg gcg cgc     1009
Ala Val Leu Gly Gly Leu Gly Gln Phe Gly Val Ile Thr Arg Ala Arg
235                 240                 245 atc ccg ctc gcg ccg gcg ccg gcg agg gcg cgg tgg gtg cgg ttc gtg     1057
Ile Pro Leu Ala Pro Ala Pro Ala Arg Ala Arg Trp Val Arg Phe Val
250                 255                 260                 265 tac acg acg gcg gcg gcg atg acg gcc gac cag gag cgc ctc atc gcc     1105
Tyr Thr Thr Ala Ala Ala Met Thr Ala Asp Gln Glu Arg Leu Ile Ala
                270                 275                 280 gtc gat cgc gcc ggc ggc gcc ggc gcg gtg ggc ggg ctg atg gac tac     1153
Val Asp Arg Ala Gly Gly Ala Gly Ala Val Gly Gly Leu Met Asp Tyr
            285                 290                 295 gtc gag ggc tcg gtc cac ctg aac cag ggc ctg gtc gag acc tgg cgc     1201
Val Glu Gly Ser Val His Leu Asn Gln Gly Leu Val Glu Thr Trp Arg
                300                 305                 310 acg cag ccg cag ccg cct tcg ccg tcc tcc tcc tcc tca tcc ttc         1249
Thr Gln Pro Gln Pro Pro Ser Pro Ser Ser Ser Ser Ser Ser Phe
315                 320                 325 ttc tcc gac gcc gac gag gcc cgc gtc gcc gcg ctc gcc aag gag gcc     1297
Phe Ser Asp Ala Asp Glu Ala Arg Val Ala Ala Leu Ala Lys Glu Ala
330                 335                 340                 345 ggc ggc gtg ctg tat ttc ctc gag ggc gcc atc tac ttc ggc ggc gcc     1345
Gly Gly Val Leu Tyr Phe Leu Glu Gly Ala Ile Tyr Phe Gly Gly Ala
            350                 355                 360 gcc ggg ccg tcc gcc gcc gac gtt gac aag gtatactagc tagctactag       1395
Ala Gly Pro Ser Ala Ala Asp Val Asp Lys
                365                 370 cttgctctgc gctgagccga ccagagcggg tcccacctcg tgatgatggc gggaacaact   1455
aagctgcaaa aacttttggc gccacctggg gcttacgctt acgcacgcat gcaattaagg   1515
ggtgttctag atggggctaa aacttttttag cccatgtcac atcggatgtt tggacgctaa  1575
tttggagtat taaatataga ctaataaaaa aactaatttc ataaatgaga gctaatccgc   1635
gagacgaatt ttttaagcct aattaatcta taattataaa agtttattgt agcatcacat   1695
tgtcaaaatc atgacataat tagactcaaa agattcgtct cgtgaattag tccaagatat   1755
ggaatatgtt ttataattag tgtatgttta atactccaaa ttagtattca aacatctggt   1815
gtgacatgga cttggaataa gtccgtggaa accaaacaga ccctaacggt gcatgaaatt   1875
gaagtctctt gcgccgtcga catcgtcgta cttggcctac cacttttgtc tgccacgcga   1935
tgcacctctc gctatcacac acctaactgg aagtaattaa ataattattc gattctgtgt   1995 taatttttt ttatcttcct tagttcccgg agagacaaag attagatact atagtagcaa    2055
cttagtaagc tagtatatgg agtattaggt tagtcgctct cactaagctt aaacaggtgt   2115
ataaaatata tgcatcgtct gatcgtgaca tattctttta gctacttatg gtgaaaactt   2175
tttcgtccaa aacagtgaaa agcatgcgtg ctagtgtagg tagtagctac caggacgaat   2235
```

-continued

```
tatatcatta acagtatttg tagcacatca aggaaaaact tgtcttttta aacactgtta    2295
cagtcttcag aacgcacaac tttaacaggt attttgtat tatattttt taaaaaaaa      2355 taaaggtaat aaaattatgg tattgtaaaa gtatatttt aaggaaaatc atataaccaa    2415
tcaaaagttt atgaagatat acatattgat gttcaaagtt actaaaagtt gacttaaaca    2475
tcacattttc atcttgacca agagggttc atatatatac tccctcaatt ttaaaatata    2535
agcatttcta attatatgca tctagacaaa tgcatataaa aatactttat tttttaaagt    2595
gagggagtat caattttgag catgtagcta gactagatta gtgtatgtct acgcacatat    2655
ctgttgttct gcacaaaact actactcatc ggtcctaaaa tataagaatt taaaattgga    2715
tgggacatac cctaatacaa tgaatttaga catggacata tactagtaat accatgtact    2775
acctccatcc caaaataagt tcacttttca tccatctcac ataccaat agaaagtact     2835 acaaatttcg gttattctct attttcacaa actccgatgc aatgattatt ttaaaaataa    2895
acttatttta gaataaatgg aatgagcaaa atataaactg gtgtgtttga ggagaagggg    2955
attgaggaga ttgggaagat acgcaaaacg aggtgagcca ttagctcatg attaattgag    3015
tattaactat tttaaatttc aaaaatggat taatatgatt ttttaaagca actttcctat    3075
ataaaatttt tacaaaaaac acacgtttta atagtttgga aagcgtactt gcggaaaacg    3135
aggtgctttc tccctcaatg tcgtccaaac gaacgctgcc ttattacggg actgaggaat    3195
tagagctttg ccagaaagaa atcagcatcg ccagcttgga cctaccatcc atgcatgcat    3255
catgtggcca ttgacacatc acatagtatg tgctagctag ctagcttttg atcatagtta    3315
catgtatcta gctaggctag aagctggaaa ccgatggata tgatggatct ctcatggatg    3375
acaggccagc caaagatctg tgcgccacta gatacagtgc atgcatcagc ttgtatggtt    3435
ataaccctag ctagccagct ttagcacaca catgcatatg catgcatgag cccccatctt    3495
ttgcaacacg accgaccaac tatgttggct ctatatagat agctagctag ttattccatg    3555
catatacagt ttgcatttcc tagctatagc ttttgctatg tgatccgaga agatcctgca    3615
tgcccacacg tgacacgtca cacacacatg tggacaaagt actgcctcac tttatccttg    3675
catgacgtca cgtcgccacc tgtccatcca cgctgctagt gctggcaaaa ttaataactc    3735
gatcaaattt cggtgatctc tctgcaaaga atttgatgaa ttttaccaac atatatgctt    3795
```

| | | | |
|---|---|---|---|
| taatttcttt gcttgatttt atttgcag agg atg gat gtg ctg cgt cgc gag | | | 3847 |
|                                            Arg Met Asp Val Leu Arg Arg Glu | | | |
|                                                          375 | | | |

```
ctg cgg cac gag cgc ggg ttc gtg ttc gcg cag gac gtg gcg tac gcc    3895
Leu Arg His Glu Arg Gly Phe Val Phe Ala Gln Asp Val Ala Tyr Ala
380             385                 390                 395 ggg ttc ctg gac cgc gtc cac gac ggc gag ctc aag ctc cgc gcc gcg    3943
Gly Phe Leu Asp Arg Val His Asp Gly Glu Leu Lys Leu Arg Ala Ala
                400                 405                 410 ggg ctc tgg gac gtg ccg cac cca tgg ctg aac ctg ttc ctc ccc cgc    3991
Gly Leu Trp Asp Val Pro His Pro Trp Leu Asn Leu Phe Leu Pro Arg
            415                 420                 425 tcc ggc gtc ctc gcc ttc gcc gac ggc gtc ttc cac ggc atc ctc agc    4039
Ser Gly Val Leu Ala Phe Ala Asp Gly Val Phe His Gly Ile Leu Ser
        430                 435                 440 cgc acc ccc gcc atg ggc ccc gtc ctc atc tac ccc atg aac cgc aac    4087
Arg Thr Pro Ala Met Gly Pro Val Leu Ile Tyr Pro Met Asn Arg Asn
    445                 450                 455 aag taataataat aataaaaagc tttactacat atacacatgt atataatttt           4140
Lys
```

-continued

```
460 tacggggtgg attttttcgt tcaaaatgac gacccctcat attgtgcgtg tcgtctgaaa    4200 acttattaaa atgtttaaat aaaaaattaa tatgatacat aaatatatta tatatcacta    4260 tataaacatt gtaatcttaa actcaacttg cacaagtagt aaaaaaacaa atttgactgc    4320 aaatagtgtg tactaagtta tttatttact tatgctagta tgctacttga atttaaacgt    4380 acatatttat gaagtggtat attatatatt tccagagtat ttttatggtt cttttacgac    4440 atgaaaaaca atgtccgttc tcttgaagga tgaatagact ttccttaatt ttaacatata    4500 tggtggtaac taaacataca cacacctgga tatgtttcag g tgg gac agt aac atg   4556
                                              Trp Asp Ser Asn Met
                                                              465 tcg gca gtg atc acc gac gac gac ggt gac gag gtg ttc tac acg gtg    4604
Ser Ala Val Ile Thr Asp Asp Asp Gly Asp Glu Val Phe Tyr Thr Val
                470                 475                 480 ggg atc ctg cgg tcg gcg gcg gcg gcc ggc gac gtg ggg agg ctg gag    4652
Gly Ile Leu Arg Ser Ala Ala Ala Ala Gly Asp Val Gly Arg Leu Glu
            485                 490                 495 gag cag aac gac gag atc ttg ggt ttc tgc gag gtg gcc ggg ata gcc    4700
Glu Gln Asn Asp Glu Ile Leu Gly Phe Cys Glu Val Ala Gly Ile Ala
        500                 505                 510 tac aag cag tac ctg cct tac tac ggc agc cag gca gag tgg cag aag    4748
Tyr Lys Gln Tyr Leu Pro Tyr Tyr Gly Ser Gln Ala Glu Trp Gln Lys
    515                 520                 525 cgg cac ttc ggt gcc aat ctc tgg cca aga ttc gtg cag cgg aag agc    4796
Arg His Phe Gly Ala Asn Leu Trp Pro Arg Phe Val Gln Arg Lys Ser
530                 535                 540                 545 aag tat gat cca aag gcc atc ctg tcc cgt ggc cag ggg att ttc acg    4844
Lys Tyr Asp Pro Lys Ala Ile Leu Ser Arg Gly Gln Gly Ile Phe Thr
                550                 555                 560 tca cca ctc gca tgaaatgaca catgtatgca aatgcatatc tacatgcgta        4896
Ser Pro Leu Ala
            565 tatatacacg tatatatacg tatgtatgca tacacatatg ggtgtactgt gcatacgtta    4956 tagcacactg cagctaatta agcttgacag ggagatcgat caatggacaa tgctctagtc    5016 aagctaatat aaataatgga gtagtagtat atatgtagtg cgagataatt aagtagtgtg    5076 tttgcctact aaaaggagag gcaaagtagt actgtgatgc atgcatgcca actaataggt    5136 gataagtacg tgtgtgtggc cgcatgtatg attagaagaa gttggttttt aattaattaa    5196 ttaggtcatg tatgtaaata tatagtacag tactacgtac tactagtgta ctaccagcca    5256 atttgcatgc atgcatggat gccttcatat gcatgtcgat ctcaaacgta cggcatgctt    5316 gaatgcatca tgatgcatat ctatcgtcgt cttgtgggtg taaactaaat taatcttagt    5376 tatatgtatt ataagtttgc aata                                          5400

<210> SEQ ID NO 2
<211> LENGTH: 2302
<212> TYPE: DNA
<213> ORGANISM: Oryza sativa

<400> SEQUENCE: 2
gcaagaacac acaaattcac acacacactg acacacacaa accgatcgat tgattgattg     60
ataatgaagc aagagcaggt caggatggca gtgctcctca tgctcaactg cttcgtcaag    120
gccacggcgc cgccgccatg gccgccgtcg gcttcgtccg cctccttcct cgacgacctc    180
ggcgacctcg gcatcgcgcc gctcatccgc gccgacgagg cgggcaccgc gcgcgcctcc    240
```

```
gccgactttg gcaacctctc cgtcgccggc gtcggggcgc ctcggctcgc cgccgccgcc      300
gccgtgctct acccgtcgcg ccccgccgac atcgccgcgc tgctgcgcgc gtcgtgcgca      360
cgcccggcgc cgttcgcggt gtccgcgcgg gggtgtggcc actcggtgca cggccaggcc      420
tccgcgcccg acggcgtcgt cgtcgacatg gcgtcgctcg gccgcctgca gggcggcggc      480
gcgcggcgcc tcgccgtgtc agtggagggg cggtacgtcg acgccggcgg cgagcagctg      540
tgggtggacg tgctgcgcgc gtccatggcg cacgggctca cgccggtgtc gtggacagac      600
tacctccacc tcaccgtcgg cggcacgctg tccaacgccg gcatcagcgg ccaggccttc      660
cgccatggcc cccagatttc caacgtgcta gagctcgacg tcatcaccgg tgtcggggag      720
atggtgacgt gctcgaagga gaaggcgccg gacctgttcg acgcggtgct gggcgggctg      780
gggcagttcg gcgtcatcac gcgggcgcgc atcccgctcg cgccggcgcc ggcgagggcg      840
cggtgggtgc ggttcgtgta cacgacgcg gcggcgatga cggccgacca ggagcgcctc      900
atcgccgtcg atcgcgccgg cggcgccggc gcggtgggcg ggctgatgga ctacgtcgag      960
ggctcggtcc acctgaacca gggcctggtc gagacctggc gcacgcagcc gcagccgcct     1020
tcgccgtcct cctcctcctc ctcatccttc ttctccgacg ccgacgaggc ccgcgtcgcc     1080
gcgctcgcca aggaggccgg cggcgtgctg tatttcctcg agggcgccat ctacttcggc     1140
ggcgccgccg ggccgtccgc cgccgacgtt gacaagagga tggatgtgct cgtcgcgag     1200 ctgcggcacg agcgcgggtt cgtgttcgcg caggacgtgg cgtacgccgg gttcctggac     1260
cgcgtccacg acggcgagct caagctccgc gccgcgggc tctgggacgt gccgcaccca     1320
tggctgaacc tgttcctccc ccgctccggc gtcctcgcct tcgccgacgg cgtcttccac     1380
ggcatcctca gccgcacccc cgccatgggc cccgtcctca tctacccat gaaccgcaac     1440 aagtgggaca gtaacatgtc ggcagtgatc accgacgacg acggtgacga ggtgttctac     1500
acggtgggga tcctgcggtc ggcggcgcg gccggcgacg tggggaggct ggaggagcag     1560
aacgacgaga tcttgggttt ctgcgaggtg gccgggatag cctacaagca gtacctgcct     1620
tactacggca gccaggcaga gtggcagaag cggcacttcg gtgccaatct ctggccaaga     1680
ttcgtgcagc ggaagagcaa gtatgatcca aaggccatcc tgtcccgtgg ccaggggatt     1740
ttcacgtcac cactcgcatg aaatgacaca tgtatgcaaa tgcatatcta catgcgtata     1800
tatacacgta tatatacgta tgtatgcata cacatatggg tgtactgtgc atacgttata     1860
gcacactgca gctaattaag cttgacaggg agatcgatca atggacaatg ctctagtcaa     1920
gctaatataa ataatggagt agtagtatat atgtagtgcg agataattaa gtagtgtgtt     1980
tgcctactaa aaggagaggc aaagtagtac tgtgatgcat gcatgccaac taataggtga     2040
taagtacgtg tgtgtggccg catgtatgat tagaagaagt tggttttaa ttaattaatt     2100 aggtcatgta tgtaaatata tagtacagta ctacgtacta ctagtgtact accagccaat     2160
ttgcatgcat gcatggatgc cttcatatgc atgtcgatct caaacgtacg gcatgcttga     2220
atgcatcatg atgcatatct atcgtcgtct tgtgggtgta aactaaatta atcttagtta     2280
tatgtattat aagtttgcaa ta                                              2302
```

<210> SEQ ID NO 3
<211> LENGTH: 565
<212> TYPE: PRT
<213> ORGANISM: Oryza sativa

<400> SEQUENCE: 3

-continued

```
Met Lys Gln Glu Gln Val Arg Met Ala Val Leu Leu Met Leu Asn Cys
1               5                   10                  15

Phe Val Lys Ala Thr Ala Pro Pro Trp Pro Ser Ala Ser Ser
            20              25              30

Ala Ser Phe Leu Asp Asp Leu Gly Asp Leu Gly Ile Ala Pro Leu Ile
        35                  40                  45

Arg Ala Asp Glu Ala Gly Thr Ala Arg Ala Ser Ala Asp Phe Gly Asn
50                      55                  60

Leu Ser Val Ala Gly Val Gly Ala Pro Arg Leu Ala Ala Ala Ala
65                  70              75                      80

Val Leu Tyr Pro Ser Arg Pro Ala Asp Ile Ala Ala Leu Leu Arg Ala
                85                  90                  95

Ser Cys Ala Arg Pro Ala Pro Phe Ala Val Ser Ala Arg Gly Cys Gly
            100                 105                 110

His Ser Val His Gly Gln Ala Ser Ala Pro Asp Gly Val Val Asp
        115                 120                 125

Met Ala Ser Leu Gly Arg Leu Gln Gly Gly Ala Arg Arg Leu Ala
130                 135                 140

Val Ser Val Glu Gly Arg Tyr Val Asp Ala Gly Gly Glu Gln Leu Trp
145                 150                 155                 160

Val Asp Val Leu Arg Ala Ser Met Ala His Gly Leu Thr Pro Val Ser
                165                 170                 175

Trp Thr Asp Tyr Leu His Leu Thr Val Gly Gly Thr Leu Ser Asn Ala
                180                 185                 190

Gly Ile Ser Gly Gln Ala Phe Arg His Gly Pro Gln Ile Ser Asn Val
        195                 200                 205

Leu Glu Leu Asp Val Ile Thr Gly Val Gly Glu Met Val Thr Cys Ser
210                 215                 220

Lys Glu Lys Ala Pro Asp Leu Phe Asp Ala Val Leu Gly Gly Leu Gly
225                 230                 235                 240

Gln Phe Gly Val Ile Thr Arg Ala Arg Ile Pro Leu Ala Pro Ala Pro
                245                 250                 255

Ala Arg Ala Arg Trp Val Arg Phe Val Tyr Thr Thr Ala Ala Ala Met
            260                 265                 270

Thr Ala Asp Gln Glu Arg Leu Ile Ala Val Asp Arg Ala Gly Gly Ala
        275                 280                 285

Gly Ala Val Gly Gly Leu Met Asp Tyr Val Glu Gly Ser Val His Leu
290                 295                 300

Asn Gln Gly Leu Val Glu Thr Trp Arg Thr Gln Pro Gln Pro Pro Ser
305                 310                 315                 320

Pro Ser Ser Ser Ser Ser Ser Phe Phe Ser Asp Ala Asp Glu Ala
                325                 330                 335

Arg Val Ala Ala Leu Ala Lys Glu Ala Gly Gly Val Leu Tyr Phe Leu
            340                 345                 350

Glu Gly Ala Ile Tyr Phe Gly Gly Ala Ala Gly Pro Ser Ala Ala Asp
        355                 360                 365

Val Asp Lys Arg Met Asp Val Leu Arg Arg Glu Leu Arg His Glu Arg
370                 375                 380

Gly Phe Val Phe Ala Gln Asp Val Ala Tyr Ala Gly Phe Leu Asp Arg
385                 390                 395                 400

Val His Asp Gly Glu Leu Lys Leu Arg Ala Ala Gly Leu Trp Asp Val
            405                 410                 415

Pro His Pro Trp Leu Asn Leu Phe Leu Pro Arg Ser Gly Val Leu Ala
```

-continued

```
                420             425             430
Phe Ala Asp Gly Val Phe His Gly Ile Leu Ser Arg Thr Pro Ala Met
            435                 440                 445
Gly Pro Val Leu Ile Tyr Pro Met Asn Arg Asn Lys Trp Asp Ser Asn
        450                 455                 460
Met Ser Ala Val Ile Thr Asp Asp Gly Asp Glu Val Phe Tyr Thr
465             470                 475                 480
Val Gly Ile Leu Arg Ser Ala Ala Ala Gly Asp Val Gly Arg Leu
                485                 490                 495
Glu Glu Gln Asn Asp Glu Ile Leu Gly Phe Cys Glu Val Ala Gly Ile
            500                 505                 510
Ala Tyr Lys Gln Tyr Leu Pro Tyr Tyr Gly Ser Gln Ala Glu Trp Gln
        515                 520                 525
Lys Arg His Phe Gly Ala Asn Leu Trp Pro Arg Phe Val Gln Arg Lys
        530                 535                 540
Ser Lys Tyr Asp Pro Lys Ala Ile Leu Ser Arg Gly Gln Gly Ile Phe
545                 550                 555                 560
Thr Ser Pro Leu Ala
            565

<210> SEQ ID NO 4
<211> LENGTH: 5003
<212> TYPE: DNA
<213> ORGANISM: Oryza sativa
<220> FEATURE:
<221> NAME/KEY: CDS
<222> LOCATION: (48)..(686)
<220> FEATURE:
<221> NAME/KEY: CDS
<222> LOCATION: (778)..(1245)
<220> FEATURE:
<221> NAME/KEY: CDS
<222> LOCATION: (3425)..(3691)
<220> FEATURE:
<221> NAME/KEY: CDS
<222> LOCATION: (4143)..(4457)
<220> FEATURE:
<221> NAME/KEY: Exon
<222> LOCATION: (1)..(687)
<220> FEATURE:
<221> NAME/KEY: Intron
<222> LOCATION: (688)..(778)
<220> FEATURE:
<221> NAME/KEY: Exon
<222> LOCATION: (779)..(1245)
<220> FEATURE:
<221> NAME/KEY: Intron
<222> LOCATION: (1246)..(3424)
<220> FEATURE:
<221> NAME/KEY: Exon
<222> LOCATION: (3425)..(3690)
<220> FEATURE:
<221> NAME/KEY: Intron
<222> LOCATION: (3691)..(4141)
<220> FEATURE:
<221> NAME/KEY: Exon
<222> LOCATION: (4142)..(5003)
<220> FEATURE:
<221> NAME/KEY: modified_base
<222> LOCATION: (4037)..(4062)
<223> OTHER INFORMATION: a, c, g, or t

<400> SEQUENCE: 4
gcaagaacac acaaattcac acacacactg acacacacaa attgata atg aag caa      56
                                                    Met Lys Gln
                                                      1 gag cag gtc agg atg gca gtg ctc ctc atg ctc aac tgc ttc gtc aag    104
```

-continued

| | | |
|---|---|---|
| Glu Gln Val Arg Met Ala Val Leu Leu Met Leu Asn Cys Phe Val Lys<br>5                      10                     15 | |
| gcc acg gcg ccg ccg cca tgg ccg ccg tcg gct tcg tcc gcc tcc ttc<br>Ala Thr Ala Pro Pro Pro Trp Pro Pro Ser Ala Ser Ser Ala Ser Phe<br>20                   25                 30                     35 | 152 |
| ctc gac gac ctc ggc gac ctc ggc atc gcg ccg ctc atc cgc gcc gac<br>Leu Asp Asp Leu Gly Asp Leu Gly Ile Ala Pro Leu Ile Arg Ala Asp<br>                     40                   45                   50 | 200 |
| gag gcg gcc acc gcg cgc gcc tcc gcc gac ttt ggc aac ctc tcc gtc<br>Glu Ala Ala Thr Ala Arg Ala Ser Ala Asp Phe Gly Asn Leu Ser Val<br>                55                   60                   65 | 248 |
| gcc ggc gtc ggg gcg cct cgg ctc gcc gcc gcc gtg ctc tac ccg tcg<br>Ala Gly Val Gly Ala Pro Arg Leu Ala Ala Ala Val Leu Tyr Pro Ser<br>70                      75                     80 | 296 |
| cgc ccc gcc gac atc gcc gcg ctg ctg cgc gcg tcg tgc gca cgc ccg<br>Arg Pro Ala Asp Ile Ala Ala Leu Leu Arg Ala Ser Cys Ala Arg Pro<br>85                      90                     95 | 344 |
| gcg ccg ttc gcg gtg tcc gcg cgg ggg tgt ggc cac tcg gtg cgc ggc<br>Ala Pro Phe Ala Val Ser Ala Arg Gly Cys Gly His Ser Val Arg Gly<br>100                  105                 110                 115 | 392 |
| cag gcc tcc gcg ccc gac ggc gtc gtc gtc gac atg gcg tcg ctc ggc<br>Gln Ala Ser Ala Pro Asp Gly Val Val Val Asp Met Ala Ser Leu Gly<br>                 120                 125                 130 | 440 |
| cgc ctg cag ggc ggc ggc gcg cgg cgc ctc gcc gtg tca gtg gag ggg<br>Arg Leu Gln Gly Gly Gly Ala Arg Arg Leu Ala Val Ser Val Glu Gly<br>135                  140                 145 | 488 |
| cgg tac gtc gac gcc ggc ggc gag cag ctg tgg gtg gac gtg ctg cgc<br>Arg Tyr Val Asp Ala Gly Gly Glu Gln Leu Trp Val Asp Val Leu Arg<br>       150                 155                 160 | 536 |
| gcg tcc atg gcg cac ggg ctc acg ccg gtg tcg tgg aca gac tac ctc<br>Ala Ser Met Ala His Gly Leu Thr Pro Val Ser Trp Thr Asp Tyr Leu<br>165                  170                 175 | 584 |
| cac ctc acc gtc ggc ggc acg ctg tcc aac gcc ggc atc agc ggc cag<br>His Leu Thr Val Gly Gly Thr Leu Ser Asn Ala Gly Ile Ser Gly Gln<br>180                  185                 190                 195 | 632 |
| gcc ttc cgc cat ggc ccc cag att tcc aac gtg cta gag ctc gac gtc<br>Ala Phe Arg His Gly Pro Gln Ile Ser Asn Val Leu Glu Leu Asp Val<br>                 200                 205                 210 | 680 |
| atc acc ggtacgtaga tccatcacat ctactaagac acgcgccgcc atgatcgagg<br>Ile Thr | 736 |
| taattaaggt ataggtgttt tgacgtatac atgtatctgc a ggt gtc ggg gag atg<br>                                                                   Gly Val Gly Glu Met<br>                                                                          215 | 792 |
| gtg acg tgc tcg aag gag aag gcg ccg gac ctg ttc gac gcg gtg ctg<br>Val Thr Cys Ser Lys Glu Lys Ala Pro Asp Leu Phe Asp Ala Val Leu<br>220                      225                     230 | 840 |
| ggc ggg ctg ggg cag ttc ggc gtc atc acg cgg gcg cgc atc ccg ctc<br>Gly Gly Leu Gly Gln Phe Gly Val Ile Thr Arg Ala Arg Ile Pro Leu<br>235                  240                 245                 250 | 888 |
| gcg ccg gcg ccg gcg agg gcg cgg tgg gtg cgg ttc gtg tac acg acg<br>Ala Pro Ala Pro Ala Arg Ala Arg Trp Val Arg Phe Val Tyr Thr Thr<br>                 255                 260                 265 | 936 |
| gcg gcg gcg atg acg gcc gac cag gag cgc ctc atc gcc gtc gat cgc<br>Ala Ala Ala Met Thr Ala Asp Gln Glu Arg Leu Ile Ala Val Asp Arg<br>                 270                 275                 280 | 984 |
| gcc ggc ggc gcc ggc gcg gtg ggc ggg ctg atg gac tac gtc gag ggc<br>Ala Gly Gly Ala Gly Ala Val Gly Gly Leu Met Asp Tyr Val Glu Gly<br>285                  290                 295 | 1032 |
| tcg gtc cac ctg aac cag ggc ctg gtc gag acc tgg cgc acg cag ccg | 1080 |

```
Ser Val His Leu Asn Gln Gly Leu Val Glu Thr Trp Arg Thr Gln Pro
    300                 305                 310 cag ccg cct tcg ccg tcc tcc tcc tcc tca tcc ttc ttc tcc gac         1128
Gln Pro Pro Ser Pro Ser Ser Ser Ser Ser Ser Phe Phe Ser Asp
315                 320                 325                 330 gcc gac gag gcc cgc gtc gcc gcg ctc gcc aag gag gcc ggc ggc gtg     1176
Ala Asp Glu Ala Arg Val Ala Ala Leu Ala Lys Glu Ala Gly Gly Val
                335                 340                 345 ctg tat ttc ctc gag ggc gcc atc tac ttc ggc ggc gcc gcc ggg ccg     1224
Leu Tyr Phe Leu Glu Gly Ala Ile Tyr Phe Gly Gly Ala Ala Gly Pro
            350                 355                 360 tcc gcc gcc gac gtt gac aag gtatactagc tagctactag cttgctctgc        1275
Ser Ala Ala Asp Val Asp Lys
            365
```

| | |
|---|---|
| gctgcgccga ccagagcggg tcccacctcg tgatgatggc gggaacaact aagctgcaaa | 1335 |
| aacttttggc gccacctggg gcttacgctt acgcacgcat gcaattaagg gggtgttcag | 1395 |
| atcgggctgc ccatgtcaca tcggatgttt agacgctaat ttagagtatt aaacatagac | 1455 |
| taataaaaaa actaatttca taaatgagag ttatccgcga gacgaatttt ttaagcacaa | 1515 |
| ttaatctata attataaaaa gtttactgta gcatcacatt gtcaaaatca tgatataatt | 1575 |
| agactcaaag attcgtctca tgaattagtc caagaatata gaatgtgttt tataattagt | 1635 |
| gtatgtttat tagtatccaa acatccgatg tgatatggac ttagaataag ttttccaaac | 1695 |
| aggacctaac ggtgcatgaa attgaagtct cttgcgccgt cgacatcgtc gtacttggcc | 1755 |
| taccactttt gtctgccacg cgatgcacct ctcgctatca cacacctaac tggaagtaat | 1815 |
| taaataatta ttcgattctg tgttaatttt ttttatctt ccttagttct cggagagaca | 1875 |
| aagattagat actatagtag caacttagta agctagtata tggagtatta ggttagtcgc | 1935 |
| tctcactaag cttaaacagg tgtataaaat atatgcatcg tctgatcgtg acatattctt | 1995 |
| ttagctactt atggtgaaaa ctttttcgtc caaacagtg aaaagcatgc atgctagtgt | 2055 |
| aggtagtagc taccaggacg aattatatca ttaacagtat ttgtagcaca tcaaggaaaa | 2115 |
| acttgtctt ttaaacactg ttacagtctt cagaacgcac aactttaaca ggtattttg | 2175 |
| tattatattt ttttaaaaaa aataaaggta ataaaattat ggtattgtaa agtatattt | 2235 |
| ttaaggaaaa tcatataacc aatcaaaagt ttatgaagat atacatattg atgttcaaag | 2295 |
| ttactaaaag ttgacttaaa catcacattt tcatcttgac caaagagggt tcatatatat | 2355 |
| actccctcaa ttttaaaata taagcatttc taattatatg catctagaca aatacatata | 2415 |
| aatatacttt attttttaaa gtgagggagt atcaattttg agcatgtagc tagactagat | 2475 |
| tagtgtatgt ctacgcacat atctgttgat ctgcacaaaa ctactactca tctatcctaa | 2535 |
| aatataagaa tttaaaattg gatgggacat accctaatac aatgaatcta gacatggaca | 2595 |
| tatactagta ataccatgta ctatctccat cccaaaataa gttcactttt catccatctc | 2655 |
| atacatatac caatagaaag tactaaaaat ttcggttatt ctctattttc acaaactccg | 2715 |
| atgcaatgat tattttaaaa ataaacttat tttagaataa atggaatgag caaaatataa | 2775 |
| acttattacg ggactgagga attagagctt tgccagaaag aaatcagcat cgccagcttg | 2835 |
| gacctaccat ccatgcatgc atcatgtggc cattgcacaca tcacatagta tgtgctagct | 2895 |
| agctagcttt tgatcatagt tacatgtatc tagctaggct agaagctgga aaccgatgga | 2955 |
| tatgatggat ctctcatgga tgacaggcca gccaaagatc tgtgcgccac tagatacagt | 3015 |
| gcatgcatca gcttgtatgg ttataaccct agctagccag ctttagcaca cacatgcata | 3075 |

-continued

```
tgcatgatga gcccccatct tttgcaacac gaccgaccaa ctatgttggc catatataga    3135
tagctagcta gttattccat gcatatacag tttgcatttc ctagctatag cttttgctat    3195
gtgatccgag aagatcctgc atgcccacac gtgacacgtc acacacacat gtggacaaag    3255
tactgcctca ctttatcctt gcatgacgtc acgtcgccac ctgtccatcc acgctgctag    3315
tgctggcaaa attaataact cgatcaaatt tcggtgatct ctctgcaaag aatttgatga    3375
attttaccaa catatatgct ttaatttctt tgtttgattt tatttgcag agg atg gat    3433
                                                      Arg Met Asp
                                                              370 gtg ctg cgt cgc gag ctg cgg cac gag cgc ggg ttc gtg ttc gcg cag    3481
Val Leu Arg Arg Glu Leu Arg His Glu Arg Gly Phe Val Phe Ala Gln
        375                 380                 385 gac gtg gcg tac gcc ggg ttc ctg gac cgc gtc cac gac ggc gag ctc    3529
Asp Val Ala Tyr Ala Gly Phe Leu Asp Arg Val His Asp Gly Glu Leu
    390                 395                 400 aag ctc cgc gcc gcg ggg ctc tgg gac gtg ccg cac cca tgg ctg aac    3577
Lys Leu Arg Ala Ala Gly Leu Trp Asp Val Pro His Pro Trp Leu Asn
405                 410                 415                 420 ctg ttc ctc ccc cgc tcc ggc gtc ctc gcc ttc gcc gac ggc gtc ttc    3625
Leu Phe Leu Pro Arg Ser Gly Val Leu Ala Phe Ala Asp Gly Val Phe
                425                 430                 435 cac ggc atc ctc agc cgc acc ccc gcc atg ggc ccc gtc ctc atc tac    3673
His Gly Ile Leu Ser Arg Thr Pro Ala Met Gly Pro Val Leu Ile Tyr
            440                 445                 450 ccc atg aac cgc aac aag taataataat aataaacagc tttactacat           3721
Pro Met Asn Arg Asn Lys
            455 atacacatgt atataatttt tacggggtgg atttttttcgt tcaaaatgac gatccctcat   3781 attgtgcgtg tcgtctgaaa acttattaaa atgtttaaat aaaaaattaa tatgatacat   3841 aaatatatta tatatcacta tataaacatt ataatcttaa actcaacttg cacaagtagt   3901 aaaaaaacaa atttgactgc aaatagtgtg tactaagtta tttatttact tatgctagta   3961 tgctacttga atttaaacgt acatatttat gaagtggtat attatatatt tccagagtat   4021 ttttatggtt cttttnnnnn nnnnnnnnnn nnnnnnnnnn ncttgaagga tgaatagact   4081 ttccttaatt ttaacatata tggtggtaac taaacataca cacacgtgga tatgtttcag   4141 g tgg gac agt aac atg tcg gca gtg atc acc gac gac gac ggt gac gag   4190
  Trp Asp Ser Asn Met Ser Ala Val Ile Thr Asp Asp Asp Gly Asp Glu
          460                 465                 470 gtg ttc tac acg gtg ggg atc ctg cgg tcg gcg gcg gcg gcc ggc gac    4238
Val Phe Tyr Thr Val Gly Ile Leu Arg Ser Ala Ala Ala Ala Gly Asp
475                 480                 485                 490 gtg ggg agg ctg gag gag cag aac gac gag atc ttg ggt ttc tgc gag    4286
Val Gly Arg Leu Glu Glu Gln Asn Asp Glu Ile Leu Gly Phe Cys Glu
                495                 500                 505 gtg gcc ggg ata gcc tac aag cag tac ctg cct tac tac ggc agc cag    4334
Val Ala Gly Ile Ala Tyr Lys Gln Tyr Leu Pro Tyr Tyr Gly Ser Gln
            510                 515                 520 gca gag tgg cag aag cgg cac ttc ggt gcc aag ctc tgg cca aga ttc    4382
Ala Glu Trp Gln Lys Arg His Phe Gly Ala Lys Leu Trp Pro Arg Phe
        525                 530                 535 gtg cag cgg aag agc aag tat gat cca aag gcc atc ctg tcc cgt ggc    4430
Val Gln Arg Lys Ser Lys Tyr Asp Pro Lys Ala Ile Leu Ser Arg Gly
    540                 545                 550 cag ggg att ttc acg tca cca ctc gca tgaaatgaca catgtatgca           4477
Gln Gly Ile Phe Thr Ser Pro Leu Ala
555                 560
```

```
aatgcatatc tacatgcgta tatatacacg tatatatacg tatgtatgca tacacatatg      4537
ggtgtactgt gcatacgtta tagcacactg cagctaatta agcttgacag ggggagatcg      4597
atcaatggac aatgctctag tcaagctaat ataaataatg gagtagtagt atatatgtag      4657
tgcgagataa ttaagtagtg tgtttgccta ctaaaaggag aggcaaagta gtactgtgat      4717
gcatgcatgc caactaatag gtgataagta cgtgtgtgtg gccgcatgta tgattagaag      4777
aagttggttt ttaattaatt aattaggtca tgtatgtaaa tatatagtac agtactacgt      4837
actactagtg tactaccagc caatttgcat gcatgcatgg atgccttcat atgcatgtcg      4897
atctcaaacg tacggcatgc ttgaatgcat catgatgcat atctatcgtc gtcttgtggg      4957
tgtaaactaa attaatctta gttatatgta ttataagttt gcaata                    5003

<210> SEQ ID NO 5
<211> LENGTH: 2282
<212> TYPE: DNA
<213> ORGANISM: Oryza sativa

<400> SEQUENCE: 5
gcaagaacac acaaattcac acacacactg acacacacaa attgataatg aagcaagagc        60
aggtcaggat ggcagtgctc ctcatgctca actgcttcgt caaggccacg cgccgccgc        120 catggccgcc gtcggcttcg tccgcctcct tcctcgacga cctcggcgac ctcggcatcg       180
cgccgctcat ccgcgccgac gaggcggcca ccgcgcgcgc ctccgccgac tttggcaacc       240
tctccgtcgc cggcgtcggg gcgcctcggc tcgccgccgc cgtgctctac ccgtcgcgcc       300
ccgccgacat cgccgcgctg ctgcgcgcgt cgtgcgcacg cccggcgccg ttcgcggtgt       360
ccgcgcgggg gtgtggccac tcggtgcgcg gccaggcctc cgcgcccgac ggcgtcgtcg       420
tcgacatggc gtcgctcggc cgcctgcagg gcggcggcgc gcggcgcctc gccgtgtcag       480
tggaggggcg gtacgtcgac gccggcggcg agcagctgtg ggtggacgtg ctgcgcgcgt       540
ccatggcgca cgggctcacg ccggtgtcgt ggacagacta cctccacctc accgtcggcg       600
gcacgctgtc caacgccggc atcagcgcc aggccttccg ccatggcccc cagatttcca       660
acgtgctaga gctcgacgtc atcaccggtg tcggggagat ggtgacgtgc tcgaaggaga       720
aggcgccgga cctgttcgac gcggtgctgg gcgggctggg gcagttcggc gtcatcacgc       780
gggcgcgcat cccgctcgcg ccggcgccgg cgagggcgcg gtgggtgcgg ttcgtgtaca       840
cgacggcggc ggcgatgacg gccgaccagg agcgcctcat cgccgtcgat cgcgccggcg       900
gcgccggcgc ggtgggcggg ctgatggact acgtcgaggg ctcggtccac ctgaaccagg       960
gcctggtcga gacctggcgc acgcagccgc agccgccttc gccgtcctcc tcctcctcct      1020
catccttctt ctccgacgcc gacgaggccc gcgtcgccgc gctcgccaag gaggccggcg      1080
gcgtgctgta tttcctcgag ggcgccatct acttcggcgg cgccgccggg ccgtccgccg      1140
ccgacgttga caagaggatg gatgtgctgc gtcgcgagct gcggcacgag cgcgggttcg      1200
tgttcgcgca ggacgtggcg tacgccgggt tcctggaccg cgtccacgac ggcgagctca      1260
agctccgcgc cgcggggctc tgggacgtgc cgcacccatg gctgaacctg ttcctccccc      1320
gctccggcgt cctcgccttc gccgacgcg tcttccacgg catcctcagc cgcacccccg      1380
ccatgggccc cgtcctcatc tacccccatga accgcaacaa gtgggacagt aacatgtcgg      1440
cagtgatcac cgacgacgac ggtgacgagg tgttctacac ggtggggatc ctgcggtcgg      1500
cggcggcggc cggcgacgtg gggaggctgg aggagcagaa cgacgagatc ttgggttct      1560
```

-continued

```
gcgaggtggc cgggatagcc tacaagcagt acctgcctta ctacggcagc caggcagagt    1620
ggcagaagcg gcacttcggt gccaagctct ggccaagatt cgtgcagcgg aagagcaagt    1680
atgatccaaa ggccatcctg tcccgtggcc aggggatttt cacgtcacca ctcgcatgaa    1740
atgacacatg tatgcaaatg catatctaca tgcgtatata tacacgtata tatacgtatg    1800
tatgcataca catatgggtg tactgtgcat acgttatagc acactgcagc taattaagct    1860
tgacaggggg agatcgatca atggacaatg ctctagtcaa gctaatataa ataatggagt    1920
agtagtatat atgtagtgcg agataattaa gtagtgtgtt tgcctactaa aaggagaggc    1980
aaagtagtac tgtgatgcat gcatgccaac taataggtga taagtacgtg tgtgtggccg    2040
catgtatgat tagaagaagt tggtttttaa ttaattaatt aggtcatgta tgtaaatata    2100
tagtacagta ctacgtacta ctagtgtact accagccaat ttgcatgcat gcatggatgc    2160
cttcatatgc atgtcgatct caaacgtacg gcatgcttga atgcatcatg atgcatatct    2220
atcgtcgtct tgtgggtgta aactaaatta atcttagtta tatgtattat aagtttgcaa    2280
ta                                                                   2282
```

<210> SEQ ID NO 6
<211> LENGTH: 563
<212> TYPE: PRT
<213> ORGANISM: Oryza sativa

<400> SEQUENCE: 6

```
Met Lys Gln Glu Gln Val Arg Met Ala Val Leu Leu Met Leu Asn Cys
1               5                   10                  15

Phe Val Lys Ala Thr Ala Pro Pro Trp Pro Pro Ser Ala Ser Ser
                20                  25                  30

Ala Ser Phe Leu Asp Asp Leu Gly Asp Leu Gly Ile Ala Pro Leu Ile
            35                  40                  45

Arg Ala Asp Glu Ala Ala Thr Ala Arg Ala Ser Ala Asp Phe Gly Asn
        50                  55                  60

Leu Ser Val Ala Gly Val Gly Ala Pro Arg Leu Ala Ala Ala Val Leu
65                  70                  75                  80

Tyr Pro Ser Arg Pro Ala Asp Ile Ala Ala Leu Leu Arg Ala Ser Cys
                85                  90                  95

Ala Arg Pro Ala Pro Phe Ala Val Ser Ala Arg Gly Cys Gly His Ser
            100                 105                 110

Val Arg Gly Gln Ala Ser Ala Pro Asp Gly Val Val Asp Met Ala
        115                 120                 125

Ser Leu Gly Arg Leu Gln Gly Gly Ala Arg Arg Leu Ala Val Ser
    130                 135                 140

Val Glu Gly Arg Tyr Val Asp Ala Gly Gly Glu Gln Leu Trp Val Asp
145                 150                 155                 160

Val Leu Arg Ala Ser Met Ala His Gly Leu Thr Pro Val Ser Trp Thr
                165                 170                 175

Asp Tyr Leu His Leu Thr Val Gly Gly Thr Leu Ser Asn Ala Gly Ile
            180                 185                 190

Ser Gly Gln Ala Phe Arg His Gly Pro Gln Ile Ser Asn Val Leu Glu
        195                 200                 205

Leu Asp Val Ile Thr Gly Val Gly Glu Met Val Thr Cys Ser Lys Glu
    210                 215                 220

Lys Ala Pro Asp Leu Phe Asp Ala Val Leu Gly Gly Leu Gly Gln Phe
225                 230                 235                 240
```

-continued

Gly Val Ile Thr Arg Ala Arg Ile Pro Leu Ala Pro Ala Pro Ala Arg
                 245                 250                 255

Ala Arg Trp Val Arg Phe Val Tyr Thr Thr Ala Ala Ala Met Thr Ala
             260                 265                 270

Asp Gln Glu Arg Leu Ile Ala Val Asp Arg Ala Gly Ala Gly Ala Ala
         275                 280                 285

Val Gly Gly Leu Met Asp Tyr Val Glu Gly Ser Val His Leu Asn Gln
     290                 295                 300

Gly Leu Val Glu Thr Trp Arg Thr Gln Pro Gln Pro Ser Pro Ser
305                 310                 315                 320

Ser Ser Ser Ser Ser Phe Phe Ser Asp Ala Glu Ala Arg Val
                 325                 330                 335

Ala Ala Leu Ala Lys Glu Ala Gly Gly Val Leu Tyr Phe Leu Glu Gly
             340                 345                 350

Ala Ile Tyr Phe Gly Gly Ala Ala Gly Pro Ser Ala Ala Asp Val Asp
         355                 360                 365

Lys Arg Met Asp Val Leu Arg Arg Glu Leu Arg His Glu Arg Gly Phe
     370                 375                 380

Val Phe Ala Gln Asp Val Ala Tyr Ala Gly Phe Leu Asp Arg Val His
385                 390                 395                 400

Asp Gly Glu Leu Lys Leu Arg Ala Ala Gly Leu Trp Asp Val Pro His
                 405                 410                 415

Pro Trp Leu Asn Leu Phe Leu Pro Arg Ser Gly Val Leu Ala Phe Ala
             420                 425                 430

Asp Gly Val Phe His Gly Ile Leu Ser Arg Thr Pro Ala Met Gly Pro
         435                 440                 445

Val Leu Ile Tyr Pro Met Asn Arg Asn Lys Trp Asp Ser Asn Met Ser
     450                 455                 460

Ala Val Ile Thr Asp Asp Asp Gly Asp Glu Val Phe Tyr Thr Val Gly
465                 470                 475                 480

Ile Leu Arg Ser Ala Ala Ala Gly Asp Val Gly Arg Leu Glu Glu
                 485                 490                 495

Gln Asn Asp Glu Ile Leu Gly Phe Cys Glu Val Ala Gly Ile Ala Tyr
             500                 505                 510

Lys Gln Tyr Leu Pro Tyr Tyr Gly Ser Gln Ala Glu Trp Gln Lys Arg
         515                 520                 525

His Phe Gly Ala Lys Leu Trp Pro Arg Phe Val Gln Arg Lys Ser Lys
     530                 535                 540

Tyr Asp Pro Lys Ala Ile Leu Ser Arg Gly Gln Gly Ile Phe Thr Ser
545                 550                 555                 560

Pro Leu Ala

<210> SEQ ID NO 7
<211> LENGTH: 501
<212> TYPE: PRT
<213> ORGANISM: Arabidopsis thaliana

<400> SEQUENCE: 7

Met Ala Asn Leu Arg Leu Met Ile Thr Leu Ile Thr Val Leu Met Ile
1               5                   10                  15

Thr Lys Ser Ser Asn Gly Ile Lys Ile Asp Leu Pro Lys Ser Leu Asn
                20                  25                  30

Leu Thr Leu Ser Thr Asp Pro Ser Ile Ile Ser Ala Ala Ser His Asp
            35                  40                  45

```
Phe Gly Asn Ile Thr Thr Val Thr Pro Gly Gly Val Ile Cys Pro Ser
    50                  55                  60

Ser Thr Ala Asp Ile Ser Arg Leu Leu Gln Tyr Ala Ala Asn Gly Lys
65                  70                  75                  80

Ser Thr Phe Gln Val Ala Ala Arg Gly Gln Gly His Ser Leu Asn Gly
                    85                  90                  95

Gln Ala Ser Val Ser Gly Gly Val Ile Val Asn Met Thr Cys Ile Thr
                100                 105                 110

Asp Val Val Ser Lys Asp Lys Lys Tyr Ala Asp Val Ala Ala Gly
                115                 120                 125

Thr Leu Trp Val Asp Val Lys Lys Thr Ala Glu Lys Gly Val Ser
    130                 135                 140

Pro Val Ser Trp Thr Asp Tyr Leu His Ile Thr Val Gly Arg Thr Leu
145                 150                 155                 160

Ser Asn Gly Gly Ile Gly Gly Gln Val Phe Arg Asn Gly Pro Leu Val
                165                 170                 175

Ser Asn Val Leu Glu Leu Asp Val Ile Thr Gly Lys Gly Glu Met Leu
                180                 185                 190

Thr Cys Ser Arg Gln Leu Asn Pro Glu Leu Phe Tyr Gly Val Leu Gly
    195                 200                 205

Gly Leu Gly Gln Phe Gly Ile Ile Thr Arg Ala Arg Ile Val Leu Asp
    210                 215                 220

His Ala Pro Lys Arg Ala Lys Trp Phe Arg Met Leu Tyr Ser Asp Phe
225                 230                 235                 240

Thr Thr Phe Thr Lys Asp Gln Glu Arg Leu Ile Ser Met Ala Asn Asp
                245                 250                 255

Ile Gly Val Asp Tyr Leu Glu Gly Gln Ile Phe Leu Ser Asn Gly Val
                260                 265                 270

Val Asp Thr Ser Phe Phe Pro Pro Ser Asp Gln Ser Lys Val Ala Asp
                275                 280                 285

Leu Val Lys Gln His Gly Ile Ile Tyr Val Leu Glu Val Ala Lys Tyr
    290                 295                 300

Tyr Asp Asp Pro Asn Leu Pro Ile Ile Ser Lys Val Ile Asp Thr Leu
305                 310                 315                 320

Thr Lys Thr Leu Ser Tyr Leu Pro Gly Phe Ile Ser Met His Asp Val
                325                 330                 335

Ala Tyr Phe Asp Phe Leu Asn Arg Val His Val Glu Glu Asn Lys Leu
                340                 345                 350

Arg Ser Leu Gly Leu Trp Glu Leu Pro His Pro Trp Leu Asn Leu Tyr
    355                 360                 365

Val Pro Lys Ser Arg Ile Leu Asp Phe His Asn Gly Val Val Lys Asp
    370                 375                 380

Ile Leu Leu Lys Gln Lys Ser Ala Ser Gly Leu Ala Leu Leu Tyr Pro
385                 390                 395                 400

Thr Asn Arg Asn Lys Trp Asp Asn Arg Met Ser Ala Met Ile Pro Glu
                405                 410                 415

Ile Asp Glu Asp Val Ile Tyr Ile Ile Gly Leu Leu Gln Ser Ala Thr
                420                 425                 430

Pro Lys Asp Leu Pro Glu Val Glu Ser Val Asn Glu Lys Ile Ile Arg
    435                 440                 445

Phe Cys Lys Asp Ser Gly Ile Lys Ile Lys Gln Tyr Leu Met His Tyr
450                 455                 460

Thr Ser Lys Glu Asp Trp Ile Glu His Phe Gly Ser Lys Trp Asp Asp
```

-continued

```
               465                 470                 475                 480
       Phe Ser Lys Arg Lys Asp Leu Phe Asp Pro Lys Lys Leu Leu Ser Pro
                       485                 490                 495

Gly Gln Asp Ile Phe
                       500

<210> SEQ ID NO 8
<211> LENGTH: 523
<212> TYPE: PRT
<213> ORGANISM: Arabidopsis thaliana

<400> SEQUENCE: 8

Met Ala Ser Tyr Asn Leu Arg Ser Gln Val Arg Leu Ile Ala Ile Thr
1               5                   10                  15

Ile Val Ile Ile Ile Thr Leu Ser Thr Pro Ile Thr Thr Asn Thr Ser
            20                  25                  30

Pro Gln Pro Trp Asn Ile Leu Ser His Asn Glu Phe Ala Gly Lys Leu
        35                  40                  45

Thr Ser Ser Ser Ser Val Glu Ser Ala Ala Thr Asp Phe Gly His
    50                  55                  60

Val Thr Lys Ile Phe Pro Ser Ala Val Leu Ile Pro Ser Ser Val Glu
65                  70                  75                  80

Asp Ile Thr Asp Leu Ile Lys Leu Ser Phe Asp Ser Gln Leu Ser Phe
                85                  90                  95

Pro Leu Ala Ala Arg Gly His Gly His Ser His Arg Gly Gln Ala Ser
            100                 105                 110

Ala Lys Asp Gly Val Val Val Asn Met Arg Ser Met Val Asn Arg Asp
        115                 120                 125

Arg Gly Ile Lys Val Ser Arg Thr Cys Leu Tyr Val Asp Val Asp Ala
    130                 135                 140

Ala Trp Leu Trp Ile Glu Val Leu Asn Lys Thr Leu Glu Leu Gly Leu
145                 150                 155                 160

Thr Pro Val Ser Trp Thr Asp Tyr Leu Tyr Leu Thr Val Gly Gly Thr
                165                 170                 175

Leu Ser Asn Gly Gly Ile Ser Gly Gln Thr Phe Arg Tyr Gly Pro Gln
            180                 185                 190

Ile Thr Asn Val Leu Glu Met Asp Val Ile Thr Gly Lys Gly Glu Ile
        195                 200                 205

Ala Thr Cys Ser Lys Asp Met Asn Ser Asp Leu Phe Phe Ala Val Leu
    210                 215                 220

Gly Gly Leu Gly Gln Phe Gly Ile Ile Thr Arg Ala Arg Ile Lys Leu
225                 230                 235                 240

Glu Val Ala Pro Lys Arg Ala Lys Trp Leu Arg Phe Leu Tyr Ile Asp
                245                 250                 255

Phe Ser Glu Phe Thr Arg Asp Gln Glu Arg Val Ile Ser Lys Thr Asp
            260                 265                 270

Gly Val Asp Phe Leu Glu Gly Ser Ile Met Val Asp His Gly Pro Pro
        275                 280                 285

Asp Asn Trp Arg Ser Thr Tyr Tyr Pro Pro Ser Asp His Leu Arg Ile
    290                 295                 300

Ala Ser Met Val Lys Arg His Arg Val Ile Tyr Cys Leu Glu Val Val
305                 310                 315                 320

Lys Tyr Tyr Asp Glu Thr Ser Gln Tyr Thr Val Asn Glu Glu Met Glu
                325                 330                 335
```

```
Glu Leu Ser Asp Ser Leu Asn His Val Arg Gly Phe Met Tyr Glu Lys
            340                 345                 350

Asp Val Thr Tyr Met Asp Phe Leu Asn Arg Val Arg Thr Gly Glu Leu
        355                 360                 365

Asn Leu Lys Ser Lys Gly Gln Trp Asp Val Pro His Pro Trp Leu Asn
    370                 375                 380

Leu Phe Val Pro Lys Thr Gln Ile Ser Lys Phe Asp Asp Gly Val Phe
385                 390                 395                 400

Lys Gly Ile Ile Leu Arg Asn Asn Ile Thr Ser Gly Pro Val Leu Val
                405                 410                 415

Tyr Pro Met Asn Arg Asn Lys Trp Asn Asp Arg Met Ser Ala Ala Ile
            420                 425                 430

Pro Glu Glu Asp Val Phe Tyr Ala Val Gly Phe Leu Arg Ser Ala Gly
        435                 440                 445

Phe Asp Asn Trp Glu Ala Phe Asp Gln Glu Asn Met Glu Ile Leu Lys
    450                 455                 460

Phe Cys Glu Asp Ala Asn Met Gly Val Ile Gln Tyr Leu Pro Tyr His
465                 470                 475                 480

Ser Ser Gln Glu Gly Trp Val Arg His Phe Gly Pro Arg Trp Asn Ile
                485                 490                 495

Phe Val Glu Arg Lys Tyr Lys Tyr Asp Pro Lys Met Ile Leu Ser Pro
            500                 505                 510

Gly Gln Asn Ile Phe Gln Lys Ile Asn Ser Ser
        515                 520

<210> SEQ ID NO 9
<211> LENGTH: 524
<212> TYPE: PRT
<213> ORGANISM: Arabidopsis thaliana

<400> SEQUENCE: 9

Met Thr Asn Thr Leu Cys Leu Ser Leu Ile Thr Leu Ile Thr Phe Phe
1               5                   10                  15

Ile Ser Leu Thr Pro Thr Leu Ile Lys Ser Asp Glu Gly Ile Asp Val
            20                  25                  30

Phe Leu Pro Ile Ser Leu Asn Leu Thr Val Leu Thr Asp Pro Phe Ser
        35                  40                  45

Ile Ser Ala Ala Ser His Asp Phe Gly Asn Ile Thr Asp Glu Asn Pro
    50                  55                  60

Gly Ala Val Leu Cys Pro Ser Ser Thr Thr Glu Val Ala Arg Leu Leu
65                  70                  75                  80

Arg Phe Ala Asn Gly Gly Phe Ser Tyr Asn Lys Gly Ser Thr Ser Pro
                85                  90                  95

Ala Ser Thr Phe Lys Val Ala Ala Arg Gly Gln Gly His Ser Leu Arg
            100                 105                 110

Gly Gln Ala Ser Ala Pro Gly Gly Val Val Asn Met Thr Cys Leu
        115                 120                 125

Ala Met Ala Ala Lys Pro Ala Val Val Ile Ser Ala Asp Gly Thr
    130                 135                 140

Tyr Ala Asp Val Ala Ala Gly Thr Met Trp Val Asp Val Leu Lys Ala
145                 150                 155                 160

Ala Val Asp Arg Gly Val Ser Pro Val Thr Trp Thr Asp Tyr Leu Tyr
                165                 170                 175

Leu Ser Val Gly Gly Thr Leu Ser Asn Ala Gly Ile Gly Gly Gln Thr
            180                 185                 190
```

```
Phe Arg His Gly Pro Gln Ile Ser Asn Val His Glu Leu Asp Val Ile
            195                 200                 205

Thr Gly Lys Gly Glu Met Met Thr Cys Ser Pro Lys Leu Asn Pro Glu
        210                 215                 220

Leu Phe Tyr Gly Val Leu Gly Leu Gly Gln Phe Gly Ile Ile Thr
225                 230                 235                 240

Arg Ala Arg Ile Ala Leu Asp His Ala Pro Thr Arg Val Lys Trp Ser
                245                 250                 255

Arg Ile Leu Tyr Ser Asp Phe Ser Ala Phe Lys Arg Asp Gln Glu Arg
            260                 265                 270

Leu Ile Ser Met Thr Asn Asp Leu Gly Val Asp Phe Leu Glu Gly Gln
        275                 280                 285

Leu Met Met Ser Asn Gly Phe Val Asp Thr Ser Phe Phe Pro Leu Ser
290                 295                 300

Asp Gln Thr Arg Val Ala Ser Leu Val Asn Asp His Arg Ile Ile Tyr
305                 310                 315                 320

Val Leu Glu Val Ala Lys Tyr Tyr Asp Arg Thr Thr Leu Pro Ile Ile
                325                 330                 335

Asp Gln Val Ile Asp Thr Leu Ser Arg Thr Leu Gly Phe Ala Pro Gly
            340                 345                 350

Phe Met Phe Val Gln Asp Val Pro Tyr Phe Asp Phe Leu Asn Arg Val
        355                 360                 365

Arg Asn Glu Glu Asp Lys Leu Arg Ser Leu Gly Leu Trp Glu Val Pro
370                 375                 380

His Pro Trp Leu Asn Ile Phe Val Pro Gly Ser Arg Ile Gln Asp Phe
385                 390                 395                 400

His Asp Gly Val Ile Asn Gly Leu Leu Leu Asn Gln Thr Ser Thr Ser
                405                 410                 415

Gly Val Thr Leu Phe Tyr Pro Thr Asn Arg Asn Lys Trp Asn Asn Arg
            420                 425                 430

Met Ser Thr Met Thr Pro Asp Glu Asp Val Phe Tyr Val Ile Gly Leu
        435                 440                 445

Leu Gln Ser Ala Gly Gly Ser Gln Asn Trp Gln Glu Leu Glu Asn Leu
450                 455                 460

Asn Asp Lys Val Ile Gln Phe Cys Glu Asn Ser Gly Ile Lys Ile Lys
465                 470                 475                 480

Glu Tyr Leu Met His Tyr Thr Arg Lys Glu Asp Trp Val Lys His Phe
                485                 490                 495

Gly Pro Lys Trp Asp Asp Phe Leu Arg Lys Ile Met Phe Asp Pro
            500                 505                 510

Lys Arg Leu Leu Ser Pro Gly Gln Asp Ile Phe Asn
        515                 520

<210> SEQ ID NO 10
<211> LENGTH: 533
<212> TYPE: PRT
<213> ORGANISM: Oryza sativa

<400> SEQUENCE: 10

Met Ala Ala Ile Tyr Leu Leu Ile Ala Ala Leu Ile Ala Ser Ser His
1               5                   10                  15

Ala Leu Ala Ala His Gly Ala Gly Gly Val Pro Leu Ala Ala Ala
            20                  25                  30

Ala Pro Leu Pro Phe Pro Gly Asp Leu Ala Ala Ser Gly Lys Leu Arg
```

-continued

```
                 35                  40                  45
Thr Asp Pro Asn Ala Thr Val Pro Ala Ser Met Asp Phe Gly Asn Ile
 50                  55                  60
Thr Ala Ala Leu Pro Ala Ala Val Leu Phe Pro Gly Ser Pro Gly Asp
 65                  70                  75                  80
Val Ala Glu Leu Leu Arg Ala Ala Tyr Ala Ala Pro Gly Arg Pro Phe
                 85                  90                  95
Thr Val Ser Phe Arg Gly Arg Gly His Ser Thr Met Gly Gln Ala Leu
                100                 105                 110
Ala Ala Gly Gly Val Val His Met Gln Ser Met Gly Gly Gly Gly
                115                 120                 125
Ala Pro Arg Ile Asn Val Ser Ala Asp Gly Ala Tyr Val Asp Ala Gly
130                 135                 140
Gly Glu Gln Leu Trp Val Asp Val Leu Arg Ala Ala Leu Ala Arg Gly
145                 150                 155                 160
Val Ala Pro Arg Ser Trp Thr Asp Tyr Leu His Leu Thr Val Gly Gly
                165                 170                 175
Thr Leu Ser Asn Ala Gly Val Ser Gly Gln Thr Tyr Arg His Gly Pro
                180                 185                 190
Gln Ile Ser Asn Val Leu Glu Leu Asp Val Ile Thr Gly His Gly Glu
                195                 200                 205
Thr Val Thr Cys Ser Lys Ala Val Asn Ser Asp Leu Phe Asp Ala Val
210                 215                 220
Leu Gly Gly Leu Gly Gln Phe Gly Val Ile Thr Arg Ala Arg Val Ala
225                 230                 235                 240
Val Glu Pro Ala Pro Ala Arg Ala Arg Trp Val Arg Leu Val Tyr Ala
                245                 250                 255
Asp Phe Ala Ala Phe Ser Ala Asp Gln Glu Arg Leu Val Ala Ala Arg
                260                 265                 270
Pro Asp Gly Ser His Gly Pro Trp Ser Tyr Val Glu Gly Ala Val Tyr
                275                 280                 285
Leu Ala Gly Arg Gly Leu Ala Val Ala Leu Lys Ser Ser Gly Gly Phe
                290                 295                 300
Phe Ser Asp Ala Asp Ala Ala Arg Val Ala Leu Ala Ala Ala Arg
305                 310                 315                 320
Asn Ala Thr Ala Val Tyr Ser Ile Glu Ala Thr Leu Asn Tyr Ala Ala
                325                 330                 335
Asn Ala Thr Pro Ser Ser Val Asp Ala Val Ala Ala Ala Leu Gly
                340                 345                 350
Asp Ala Leu His Phe Glu Glu Gly Phe Ser Phe Ser Arg Asp Val Thr
                355                 360                 365
Tyr Glu Glu Phe Leu Asp Arg Val Tyr Gly Glu Glu Ala Leu Glu
                370                 375                 380
Lys Ala Gly Leu Trp Arg Val Pro His Pro Trp Leu Asn Leu Phe Val
385                 390                 395                 400
Pro Gly Ser Arg Ile Ala Asp Phe Asp Arg Gly Val Phe Lys Gly Ile
                405                 410                 415
Leu Gln Thr Ala Thr Asp Ile Ala Gly Pro Leu Ile Ile Tyr Pro Val
                420                 425                 430
Asn Lys Ser Lys Trp Asp Ala Ala Met Ser Ala Val Thr Pro Glu Gly
                435                 440                 445
Glu Glu Glu Val Phe Tyr Val Val Ser Leu Leu Phe Ser Ala Val Ala
                450                 455                 460
```

```
Asn Asp Val Ala Ala Leu Glu Ala Gln Asn Arg Arg Ile Leu Arg Phe
465                 470                 475                 480

Cys Asp Leu Ala Gly Ile Gly Tyr Lys Ala Tyr Leu Ala His Tyr Asp
            485                 490                 495

Ser Arg Gly Asp Trp Val Arg His Phe Gly Ala Lys Trp Asp Arg Phe
            500                 505                 510

Val Gln Arg Lys Asp Lys Tyr Asp Pro Lys Lys Leu Leu Ser Pro Gly
            515                 520                 525

Gln Asp Ile Phe Asn
        530
```

<210> SEQ ID NO 11
<211> LENGTH: 558
<212> TYPE: PRT
<213> ORGANISM: Oryza sativa

<400> SEQUENCE: 11

```
Met Ala Val Leu Leu Met Leu Asn Cys Phe Val Lys Ala Thr Ala Pro
1               5                   10                  15

Pro Pro Trp Pro Pro Ser Ala Ser Ala Ser Phe Leu Asp Asp Leu
            20                  25                  30

Gly Asp Leu Gly Ile Ala Pro Leu Ile Arg Ala Asp Glu Ala Gly Thr
            35                  40                  45

Ala Arg Ala Ser Ala Asp Phe Gly Asn Leu Ser Val Ala Gly Val Gly
        50                  55                  60

Ala Pro Arg Leu Ala Ala Ala Ala Val Leu Tyr Pro Ser Arg Pro
65                  70                  75                  80

Ala Asp Ile Ala Ala Leu Leu Arg Ala Ser Cys Ala Arg Pro Ala Pro
                85                  90                  95

Phe Ala Val Ser Ala Arg Gly Cys Gly His Ser Val His Gly Gln Ala
            100                 105                 110

Ser Ala Pro Asp Gly Val Val Val Asp Met Ala Ser Leu Gly Arg Leu
        115                 120                 125

Gln Gly Gly Gly Ala Arg Arg Leu Ala Val Ser Val Glu Gly Arg Tyr
    130                 135                 140

Val Asp Ala Gly Gly Glu Gln Leu Trp Val Asp Val Leu Arg Ala Ser
145                 150                 155                 160

Met Ala His Gly Leu Thr Pro Val Ser Trp Thr Asp Tyr Leu His Leu
                165                 170                 175

Thr Val Gly Gly Thr Leu Ser Asn Ala Gly Ile Ser Gly Gln Ala Phe
            180                 185                 190

Arg His Gly Pro Gln Ile Ser Asn Val Leu Glu Leu Asp Val Ile Thr
        195                 200                 205

Gly Val Gly Glu Met Val Thr Cys Ser Lys Glu Lys Ala Pro Asp Leu
    210                 215                 220

Phe Asp Ala Val Leu Gly Gly Leu Gly Gln Phe Gly Val Ile Thr Arg
225                 230                 235                 240

Ala Arg Ile Pro Leu Ala Pro Ala Pro Ala Arg Ala Arg Trp Val Arg
                245                 250                 255

Phe Val Tyr Thr Thr Ala Ala Ala Met Thr Ala Asp Gln Glu Arg Leu
            260                 265                 270

Ile Ala Val Asp Arg Ala Gly Gly Ala Gly Ala Val Gly Gly Leu Met
        275                 280                 285

Asp Tyr Val Glu Gly Ser Val His Leu Asn Gln Gly Leu Val Glu Thr
```

-continued

```
                    290                 295                 300

Trp Arg Thr Gln Pro Gln Pro Ser Pro Ser Ser Ser Ser Ser Ser Ser
305                 310                 315                 320

Ser Phe Phe Ser Asp Ala Asp Glu Ala Arg Val Ala Ala Leu Ala Lys
                325                 330                 335

Glu Ala Gly Gly Val Leu Tyr Phe Leu Glu Gly Ala Ile Tyr Phe Gly
            340                 345                 350

Gly Ala Ala Gly Pro Ser Ala Ala Asp Val Asp Lys Arg Met Asp Val
        355                 360                 365

Leu Arg Arg Glu Leu Arg His Glu Arg Gly Phe Val Phe Ala Gln Asp
370                 375                 380

Val Ala Tyr Ala Gly Phe Leu Asp Arg Val His Asp Gly Glu Leu Lys
385                 390                 395                 400

Leu Arg Ala Ala Gly Leu Trp Asp Val Pro His Pro Trp Leu Asn Leu
                405                 410                 415

Phe Leu Pro Arg Ser Gly Val Leu Ala Phe Ala Asp Gly Val Phe His
            420                 425                 430

Gly Ile Leu Ser Arg Thr Pro Ala Met Gly Pro Val Leu Ile Tyr Pro
        435                 440                 445

Met Asn Arg Asn Lys Trp Asp Ser Asn Met Ser Ala Val Ile Thr Asp
450                 455                 460

Asp Asp Gly Asp Glu Val Phe Tyr Thr Val Gly Ile Leu Arg Ser Ala
465                 470                 475                 480

Ala Ala Ala Gly Asp Val Gly Arg Leu Glu Glu Gln Asn Asp Glu Ile
                485                 490                 495

Leu Gly Phe Cys Glu Val Ala Gly Ile Ala Tyr Lys Gln Tyr Leu Pro
            500                 505                 510

Tyr Tyr Gly Ser Gln Ala Glu Trp Gln Lys Arg His Phe Gly Ala Asn
        515                 520                 525

Leu Trp Pro Arg Phe Val Gln Arg Lys Ser Lys Tyr Asp Pro Lys Ala
530                 535                 540

Ile Leu Ser Arg Gly Gln Gly Ile Phe Thr Ser Pro Leu Ala
545                 550                 555

<210> SEQ ID NO 12
<211> LENGTH: 527
<212> TYPE: PRT
<213> ORGANISM: Oryza sativa

<400> SEQUENCE: 12

Met Ala Ala Arg Cys Ser Ile Ala Phe Met Val Met Ala Ser Cys Leu
1               5                   10                  15

Ser Val Val Val Ser Gly Gly Leu Pro Gly Asp Leu Phe Ala His Ser
                20                  25                  30

Val Ala Ser Lys Leu Arg Val Asp Arg Asp Thr Thr Ala Arg Ala Ser
            35                  40                  45

Ser Asp Phe Gly Arg Ile Val Ala Ala Pro Glu Ala Val Leu His
        50                  55                  60

Pro Ala Thr Pro Ala Glu Ile Ala Glu Leu Val Arg Phe Ser Ala Ser
65                  70                  75                  80

Ser Pro Ser Pro Phe Pro Val Ala Pro Arg Gly Gln Gly His Ser Ala
                85                  90                  95

Arg Gly Gln Ser Leu Ala Pro Gly Gly Val Val Asp Met Arg Ala
            100                 105                 110
```

```
Leu Ala Ala Arg Arg Gly Arg Val Asn Val Ser Ala Gly Gly Ala Gly
            115                 120                 125

Ala Ala Pro Tyr Val Asp Ala Gly Gly Glu Gln Leu Trp Ala Asp Val
        130                 135                 140

Leu Arg Ala Thr Leu Glu His Gly Leu Ala Pro Arg Val Trp Thr Asp
145                 150                 155                 160

Tyr Leu Arg Ile Thr Val Ala Gly Thr Leu Ser Asn Ala Gly Ile Gly
                165                 170                 175

Gly Gln Ala Phe Arg His Gly Pro Gln Ile Ala Asn Val Leu Glu Leu
                180                 185                 190

Asp Val Ile Thr Gly Arg Gly Asp Met Val Thr Cys Ser Arg Asp Lys
            195                 200                 205

Glu Pro Asp Leu Phe Phe Ala Val Leu Gly Leu Gly Gln Phe Gly
        210                 215                 220

Ile Ile Thr Arg Ala Arg Ile Gly Leu Glu Pro Ala Pro Lys Arg Val
225                 230                 235                 240

Arg Trp Val Arg Leu Ala Tyr Ser Asp Val Val Thr Phe Thr Arg Asp
                245                 250                 255

Gln Glu Leu Leu Ile Ser Lys Arg Ala Ser Glu Ala Gly Phe Asp Tyr
                260                 265                 270

Val Glu Gly Gln Val Gln Leu Asn Arg Thr Leu Thr Glu Gly Pro Lys
        275                 280                 285

Ser Thr Pro Phe Phe Ser Arg Phe Asp Ile Asp Arg Leu Ala Gly Leu
        290                 295                 300

Ala Ser Glu Ser Val Ser Gly Val Ile Tyr Phe Ile Glu Gly Ala Met
305                 310                 315                 320

Tyr Tyr Asn Glu Ser Thr Thr Ala Ser Val Asp Gln Lys Leu Thr Ser
                325                 330                 335

Val Leu Glu Gln Leu Ser Phe Asp Lys Gly Phe Val Phe Thr Lys Asp
                340                 345                 350

Val Ser Tyr Val Gln Phe Leu Asp Arg Val Arg Glu Glu Arg Ile
                355                 360                 365

Leu Arg Ser Ile Gly Met Trp Asp Val Pro His Pro Trp Leu Asn Leu
        370                 375                 380

Phe Val Pro Gln Ser Arg Ile Leu Asp Phe Asp Thr Gly Val Leu Lys
385                 390                 395                 400

Gly Val Phe Val Gly Ala Asn Pro Val Gly Val Ile Leu Met Tyr Pro
                405                 410                 415

Met Asn Arg Asn Met Trp Asp Asp Arg Met Thr Ala Val Ser Gly Asn
            420                 425                 430

Asp Asp Met Phe Tyr Val Val Gly Leu Leu Arg Ser Ala Val Val Pro
        435                 440                 445

Gly Asp Val Glu Arg Leu Glu Arg Glu Asn Glu Ala Val Leu Ala Phe
        450                 455                 460

Cys Asp Asn Glu Gly Ile Gly Cys Lys Gln Tyr Leu Pro His Tyr Ala
465                 470                 475                 480

Ser Gln Asp Gly Trp Arg Ser His Phe Gly Ala Lys Trp Ser Arg Val
                485                 490                 495

Thr Glu Leu Lys Val Lys Tyr Asp Pro Tyr Gly Ile Leu Ser Pro Gly
        500                 505                 510

Gln Arg Ile Phe Ser Ser Leu Thr Pro Met Ala Leu Val Ala Met
        515                 520                 525
```

<210> SEQ ID NO 13
<211> LENGTH: 524
<212> TYPE: PRT
<213> ORGANISM: Oryza sativa

<400> SEQUENCE: 13

Met Ala Ala Arg Cys Ser Ile Ala Phe Met Ile Met Ala Ser Cys Leu
1               5                   10                  15

Ser Val Val Val Ser Gly Gly Leu Pro Gly Asp Leu Phe Ala Leu Ser
            20                  25                  30

Val Ala Ser Lys Leu Arg Val Asp Arg Asn Ser Thr Ala Arg Ala Ser
        35                  40                  45

Ser Asp Phe Gly Arg Ile Val Ala Ala Pro Glu Ala Val Leu His
    50                  55                  60

Pro Ala Thr Pro Ala Glu Ile Ala Glu Leu Val Arg Phe Ser Ala Ser
65                  70                  75                  80

Ser Pro Ser Pro Phe Pro Val Ala Pro Arg Gly Gln Gly His Ser Ala
                85                  90                  95

Arg Gly Gln Ser Leu Ala Pro Gly Val Val Asp Met Arg Ala
            100                 105                 110

Leu Ala Ser Arg Arg Gly Arg Val Asn Val Ser Ala Gly Ala Ala Pro
        115                 120                 125

Tyr Val Asp Ala Gly Gly Glu Gln Leu Trp Ala Asp Val Leu Arg Ala
    130                 135                 140

Thr Leu Glu His Gly Leu Ala Pro Arg Val Trp Thr Asp Tyr Leu Arg
145                 150                 155                 160

Ile Thr Val Ala Gly Thr Leu Ser Asn Ala Gly Ile Gly Gly Gln Ala
                165                 170                 175

Phe Arg His Gly Pro Gln Ile Ala Asn Val Leu Glu Leu Asp Val Ile
            180                 185                 190

Thr Gly Thr Gly Asp Met Val Thr Cys Ser Arg Asp Lys Asp Ser Asp
        195                 200                 205

Leu Phe Phe Ala Val Leu Gly Gly Leu Gly Gln Phe Gly Ile Ile Thr
    210                 215                 220

Arg Ala Arg Ile Gly Leu Met Pro Ala Pro Lys Arg Val Arg Trp Val
225                 230                 235                 240

Arg Leu Ala Tyr Ser Asp Val Ala Thr Phe Thr Lys Asp Gln Glu Leu
                245                 250                 255

Leu Ile Ser Lys Arg Ala Ser Glu Ala Gly Phe Asp Tyr Val Glu Gly
            260                 265                 270

Gln Val Gln Leu Asn Arg Thr Leu Thr Glu Gly Pro Lys Ser Thr Pro
        275                 280                 285

Phe Phe Ser Ser Ser Asp Ile Gly Arg Leu Ala Gly Leu Ala Ser Lys
    290                 295                 300

Ser Val Ser Gly Val Ile Tyr Val Ile Glu Gly Thr Met Tyr Tyr Asn
305                 310                 315                 320

Glu Ser Thr Ser Thr Thr Met Asp Gln Lys Leu Glu Ser Ile Leu Gly
                325                 330                 335

Gln Leu Ser Phe Glu Glu Gly Phe Val Phe Thr Lys Asp Val Arg Tyr
            340                 345                 350

Val Gln Phe Leu Asp Arg Val Arg Glu Glu Arg Val Leu Arg Ser
        355                 360                 365

Ile Gly Met Trp Asp Val Pro His Pro Trp Leu Asn Leu Phe Val Pro
    370                 375                 380

-continued

```
Arg Ser Arg Ile Leu Asp Phe Asp Ala Gly Val Phe Lys Gly Val Phe
385                 390                 395                 400

Ala Gly Ala Asn Pro Val Gly Val Ile Leu Met Tyr Pro Met Asn Thr
            405                 410                 415

Asn Met Trp Asp Asp Cys Met Met Ala Val Ala Ser Asp Asp Asp Val
        420                 425                 430

Phe Tyr Ala Val Gly Leu Leu Arg Ser Ala Ala Val Ile Gly Asp Val
    435                 440                 445

Glu Arg Leu Glu Lys Glu Asn Glu Ala Val Leu Ala Phe Cys His Asn
450                 455                 460

Glu Asp Ile Gly Cys Lys Gln Tyr Leu Pro Tyr Tyr Thr Ser Gln Asp
465                 470                 475                 480

Gly Trp Gln Arg His Phe Gly Ala Lys Trp Ser Arg Val Ala Asp Leu
                485                 490                 495

Lys Ala Lys Tyr Asp Pro His Arg Ile Leu Ser Pro Gly Gln Arg Ile
            500                 505                 510

Phe Ser Ser Pro Ala Ser Met Val Val Ser Met
            515                 520

<210> SEQ ID NO 14
<211> LENGTH: 528
<212> TYPE: PRT
<213> ORGANISM: Oryza sativa

<400> SEQUENCE: 14

Met Pro Arg Ala Gln Leu Thr Thr Phe Leu Ile Val Thr Ser Phe Leu
1               5                   10                  15

Ser Thr Val Pro Tyr Leu Arg Ala Pro Val His Gly Gly Val Leu Thr
            20                  25                  30

Ser Tyr Asp Val Ser Ser Leu Asp Ile Met Ser Lys Ile His Thr Asp
        35                  40                  45

His Asp Ala Thr Thr Lys Ala Ser Ser Asp Phe Gly His Ile Val His
    50                  55                  60

Ala Thr Pro Asn Gly Val Phe Arg Pro Thr Phe Pro Ala Asp Ile Ala
65                  70                  75                  80

Ala Leu Ile Arg Leu Ser Leu Ser Gln Pro Thr Pro Phe Thr Val Ala
                85                  90                  95

Pro Arg Gly Lys Gly His Ser Ser Arg Gly Gln Ala Phe Ala Pro Gly
            100                 105                 110

Gly Ile Val Val Asp Met Ser Ala Leu Gly Asp His Gly His His Thr
        115                 120                 125

Ser His Arg Ile Asp Val Ser Val Asp Arg Met Tyr Val Asp Ala Gly
    130                 135                 140

Gly Glu Gln Leu Trp Ile Asp Val Leu His Thr Ala Leu Lys His Gly
145                 150                 155                 160

Leu Thr Pro Arg Val Trp Thr Asp Tyr Leu Arg Ile Thr Val Gly Gly
                165                 170                 175

Thr Leu Ser Asn Ala Gly Ile Gly Gly Gln Ala Phe Arg His Gly Pro
            180                 185                 190

Gln Ile Ser Asn Val His Glu Leu Asp Val Val Thr Gly Gly Leu Gly
        195                 200                 205

Gln Phe Gly Val Ile Thr Arg Ala Arg Ile Arg Leu Glu Pro Ala Pro
    210                 215                 220

Lys Arg Val Lys Trp Val Arg Ile Ala Tyr Ser Asp Val His Pro Phe
225                 230                 235                 240
```

-continued

```
Thr Thr Asp Gln Glu Leu Leu Ile Ser Lys Trp Ala Ser Gly Ser Gly
            245                 250                 255

Phe Asp Tyr Val Glu Gly Gln Val Gln Leu Asn Arg Thr Leu Thr Gln
            260                 265                 270

Gly Arg Arg Ser Ser Ser Phe Phe Ser Ala Thr Asp Leu Ala Arg Leu
            275                 280                 285

Thr Gly Leu Ala Ile Asp Thr Gly Ser Val Ala Ile Tyr Tyr Ile Glu
            290                 295                 300

Gly Ala Met Tyr Tyr Asp Asp Asn Thr Ala Ala Ser Val Asp Gln Lys
305                 310                 315                 320

Leu Asp Ala Leu Leu Glu Glu Leu Ser Phe Val Arg Gly Phe Val Phe
                    325                 330                 335

Val Arg Asp Ala Ser Tyr Val Glu Phe Leu Asp Arg Val Gly Arg Glu
                    340                 345                 350

Glu Gln Asn Leu Arg Ser Ala Gly Ala Trp Asp Val Pro His Pro Trp
            355                 360                 365

Leu Asn Leu Phe Val Pro Arg Ser Arg Ile Leu His Phe Asp Ala Ala
    370                 375                 380

Val Phe Lys Gly Ile Leu Arg Asn Ala Asn Pro Val Gly Leu Ile Leu
385                 390                 395                 400

Met Tyr Pro Met Asn Lys Asp Met Trp Asp Asp Arg Met Thr Ala Met
                    405                 410                 415

Thr Pro Asp Glu Asp Val Phe Tyr Ala Val Gly Leu Leu Arg Ser Ala
            420                 425                 430

Val Ala Gly Gly Ser Gly Gly Asp Val Glu Gln Leu Glu Arg Glu Asn
            435                 440                 445

Ala Ala Val Leu Glu Leu Cys Asp Leu Ala Gly Gly Ile Gly Cys
    450                 455                 460

Arg Gln Tyr Leu Pro His His Ala Ser Arg Asp Gly Trp Arg Arg His
465                 470                 475                 480

Phe Gly Ala Lys Trp Gly Arg Val Ala Asp Leu Lys Ala Arg Tyr Asp
                    485                 490                 495

Pro Arg Ala Ile Leu Ser Pro Gly Gln Gly Ile Phe Pro Pro Pro Pro
            500                 505                 510

Pro Pro Ser Pro Pro Pro Pro Ala Ala Gly Glu Pro Ile Thr Ala Ser
            515                 520                 525
```

GENES FOR INCREASING GRAIN YIELD AND USES THEREOF

RELATED APPLICATIONS

This application is a 35 U.S.C. §371 national stage filing of International Application No. PCT/JP03/14434, filed 13 Nov. 2003, which claims priority to U.S. Provisional Patent Application Ser. No. 60/425,919, filed 13 Nov. 2002. The contents of the aforementioned applications are hereby incorporated by reference.

TECHNICAL FIELD

The present invention relates to isolation and identification of genes that regulate the increase and decrease of the particle-bearing number (including glumous flowers, fruits, and seeds) of plants, and breeding methods that utilize these genes to increase the particle-bearing number (including glumous flowers, fruits, and seeds) of plants.

BACKGROUND ART

As the world population continues to show explosive growth, arable land is rapidly decreasing due to environmental pollution, global warming, and desertification, and chronic food shortage persists mainly in developing countries. Furthermore, the present grain production growth rate of 1.0% is low compared to the annual global population growth rate of 1.4%; furthermore, in the year 2025, when the world population is predicted to exceed eight billion, grain requirements will increase by 50%, further accelerating food shortage. In order to break this serious situation, not only political and economic measures, but also scientific grain breeding strategies that will increase the amount of grain production are necessary. This serious condition can no longer be avoided by conventional breeding, using cross-fertilization and selection techniques alone, and studies on grain plant type aimed at increasing yield, as well as specific and efficient grain breeding are necessary.

When concern was raised on world food crisis in the 1960's, short-culm high-yielding rice called miracle rice was cultivated at the International Rice Research Institute (Philippines), and short-culm high-yielding wheat was cultivated at the International Maize and Wheat Improvement Center (Mexico). World food crisis was avoided due to the rapid spread of both of these varieties. This is the so-called "Green Revolution". Both varieties showed twice the yield of conventional varieties, and this high-yielding character was caused by a short-culm plant type called a semi-dwarf. However, while application of nitrogenous fertilizers is necessary when aiming for a high yield, this simultaneously induces elongation of the plant, and lodging of the elongated grain by rain and wind dramatically decreases yield. On the other hand, even when fertilizers are applied, short-culm varieties allow an increased yield without succulent growth. That is, both short-culm varieties that contributed to the "Green Revolution" dramatically increased the yield by acquiring lodging resistance. At present, semi-dwarfism of grains greatly contributes to increased yield, but since many grain varieties already utilize semi-dwarf genes, further increase in yield using this technique cannot be expected, and development of grain production technologies that utilize new techniques is necessary.

Rice is utilized as food by 50% of the world's human population. In particular, for those living in Asia, its cultivation characteristics match the highly humid monsoon climate, and not only has it been the source of energy for a long time as the staple diet, but it has also been well established in life and culture. Accordingly, breeding has been carried out in many places, and it has been improved to have characteristics that are convenient for use by humankind. Furthermore, with the recent determination of the genomic nucleotide sequence of rice, tools for molecular genetics are being put into place, and development of new breeding technology using genomic genetics is expected.

To date, various attempts have been made to increase the yield of grains (plants); however, there are no reports of isolation and identification of genes relating to the increase and decrease of the number of flowers and seeds (glumous flowers) that are directly responsible for increase in yield. In addition to the conventional semi-dwarfing of grains, if techniques to regulate the increase and decrease in the number of flowers and seeds (glumous flowers) are developed, further increase in grain yield can be expected.

DISCLOSURE OF THE INVENTION

The present invention has been made in view of the above circumstances. An objective of this invention is to isolate and identify genes relating to the increase and decrease of the particle-bearing number (including glumous flowers, fruits, and seeds) of plants, and to provide breeding methods for increasing the particle-bearing number (including glumous flowers, fruits, and seeds) of plants, using these genes.

In an attempt to increase the grain (plant) yield, the present inventors used a rice plant, which serves as a model for a monocotyledonous plant, to search for genes that are directly responsible for increase in yield, more specifically, for genes relating to the increase and decrease of the number of flowers and seeds (glumous flowers). The number of flowers and seeds (glumous flowers) is controlled as a quantitative trait (QTL) by the interaction of more than one gene. Therefore, in order to generate a hybrid population for QTL analysis, parent varieties of the hybrids were selected. Two varieties showing a clear difference in the particle-bearing number, "Koshihikari" which is a japonica rice, and "Habataki" which is an indica rice, were selected (FIG. 1). F1 individuals produced by crossing these two varieties were backcrossed using Koshihikari as the repeated parent and self-fertilization was carried out. The resulting 74 varieties of BC2F1, BC2F2, and BC3F2 populations were cultivated and developed on the Nagoya University Farm. By performing a QTL analysis relating to the particle-bearing number using 74 BC2F2 plants, a plurality of QTL that increase the particle-bearing number was detected (FIG. 2). In particular, a QTL (YQ1; Yielding QTL 1) of Habataki, located at approximately 28 cM in the short arm of chromosome 1 (FIG. 2), was successfully discovered to be very effective in increasing the grain (or seed) number as compared to that of Koshihikari. To verify the presence of YQ1, repeated backcrossing and MAS were used to produce a YQ1 semi-isogenic line, and the maximum particle-bearing numbers of Nil-YQ 1 and Koshihikari (control) were investigated. As a result, the presence of QTL(YQ 1) was confirmed, and varieties in which the locus at approximately 28 cM in the short arm of chromosome 1 was substituted with that of Habataki were found to increase their particle-bearing number by an average of 50.

Next, from each of the 74 BC2F1 individuals, DNAs were extracted using the CTAB method, and the genotype of each individual was determined using 93 molecular markers that thoroughly cover all chromosomes. Their self-fertilized progeny, BC2F2, was developed at ten individuals per variety, and from among them, one individual per variety was randomly selected. After sampling six panicles from each of the selected individuals, the particle-bearing number was investigated for each panicle. Among the six panicles of each variety, the panicle having the largest particle-bearing number was selected, and this number was used as the maximum particle-bearing number. QTL analysis was then performed using the Qgene software.

The BC3F2 population was then used to investigate the phenotype and genotype (F2 and F3) using molecular markers, and linkage analysis was performed again. The results showed that YQ1 is located between molecular markers 6A and 8A (FIG. 3). As a result of high-resolution linkage analysis using a segregating population (12500 individuals) of YQ, the YQ1 locus was specified to be in a region of approximately 8 Kb between molecular markers 4A9 and 20 (FIG. 4). When gene prediction was performed in this region, a single gene was predicted, and, as a result of a homology search, the gene was found to be highly homologous to CKX (cytokinin oxidase) (FIG. 4). When the nucleotide sequence of this CKX gene was determined for Habataki and Koshihikari, differences in the nucleotides were found, and the CKX of Habataki seemed to have lost its function (FIG. 5).

Furthermore, when the rice genomic sequence was searched to analyze the rice CKX gene, eleven CKX genes were found to be present in the rice genome. When a phylogenic tree was constructed for these genes as well as the CKX genes in *Arabidopsis thaliana*, AtCKX2, 3, and 4 of *Arabidopsis thaliana*, and five rice CKX genes (CKX located on Chr.1 25 cM P695A4, CKX located on Chr.1 27 P419B01 (the present gene), CKX gene located on Chr.6 79 cM OsJ0006A22-GS, and two CKX genes located on Chr.2 32 cM) were found to be very closely related (FIG. 6). When the homologies of these genes were investigated, they were found to be highly homologous at the amino acid level (FIGS. 7 to 9). Furthermore, when the locus positions of all CKX genes in rice were confirmed, some of them were found to be located on the YQ regions (FIG. 10).

More specifically, the present inventors succeeded in isolating a novel gene involved in the increase and decrease of the particle-bearing number of plants, and thus completed this invention.

The present invention relates to the isolation and identification of genes that regulate the increase and decrease of the particle-bearing number (including glumous flowers, fruits, and seeds) of plants, and breeding methods that utilize these genes to increase the particle-bearing number (including glumous flowers, fruits, and seeds) of plants, and this invention provides [1] to [19] described below.

[1] A DNA encoding a plant-derived protein whose deletion of function causes an increase in the particle-bearing number of a plant, wherein the DNA is any one of (a) to (d):
(a) a DNA encoding a protein comprising the amino acid sequence of SEQ ID NO: 3;
(b) a DNA comprising a coding region comprising the nucleotide sequence of SEQ ID NO: 1 or 2;
(c) a DNA encoding a protein comprising the amino acid sequence of SEQ ID NO: 3, wherein one or more amino acids have been substituted, deleted, added, and/or inserted; and
(d) a DNA that hybridizes under stringent conditions with a DNA comprising the nucleotide sequence of SEQ ID NO: 1 or 2.
[2] The DNA of [1], wherein the DNA is derived from rice.
[3] A DNA encoding an RNA complementary to a transcript of the DNA of [1] or [2].
[4] A DNA encoding an RNA having ribozyme activity that specifically cleaves a transcript of the DNA of [1] or [2].
[5] A DNA encoding an RNA that suppresses the expression of the DNA of [1] or [2] by cosuppression effects at the time of expression in plant cells.
[6] A vector comprising the DNA of any one of [1] to [5].
[7] A host cell transfected with the vector of [6].
[8] A plant cell transfected with the vector of [6].
[9] A transformed plant comprising the plant cell of [8].
[10] A transformed plant that is an offspring or a clone of the transformed plant of [9].
[11] A reproductive material of the transformed plant of [9] or [10].
[12] A method for producing a transformed plant, wherein the method comprises the steps of introducing the DNA of any one of [1] to [5] into a plant cell, and regenerating a plant body from said plant cell.
[13] A protein encoded by the DNA of [1] or [2].
[14] A method for producing the protein of [13], wherein the method comprises the steps of culturing the host cell of [7], and collecting a recombinant protein from said cell or from a culture supernatant thereof.
[15] An antibody that binds to the protein of [13].
[16] A polynucleotide comprising at least 15 continuous nucleotides that are complementary to the nucleotide sequence of SEQ ID NO: 1 or 2, or a complementary sequence thereof.
[17] A method for increasing the particle-bearing number of a plant, wherein the method comprises the step of expressing the DNA of any one of [3] to [5] in the cells of a plant body.
[18] An agent for changing the particle-bearing number of a plant, wherein the agent comprises the DNA of any one of [1] to [5] or the vector of [6] as an active ingredient.
[19] A method for determining the particle-bearing number of a plant, wherein the method comprises the steps of:
(a) preparing a DNA sample from a test plant body, or a reproductive medium thereof;
(b) amplifying a region of said DNA sample corresponding to the DNA of [1]; and
(c) determining the nucleotide sequence of the amplified DNA region;

wherein the plant is determined to be a variety having a small particle-bearing number when the nucleotide sequence encodes a protein whose deletion of function causes an increase in the particle-bearing number of a plant, and the plant is determined to be a variety having a large particle-bearing number when said protein is not encoded.

The present invention provides DNAs that encode rice-derived CKX proteins. The genomic sequence of the DNA in "Koshihikari" is shown in SEQ ID NO: 1, its cDNA sequence is shown in SEQ ID NO: 2, and the amino acid sequence of a protein encoded by this DNA is shown in SEQ ID NO: 3. The genomic sequence of the DNA in "Habataki" is shown in SEQ ID NO: 4, its cDNA sequence is shown in SEQ ID NO: 5, and the amino acid sequence of a protein encoded by this DNA is shown in SEQ ID NO: 6.

The CKX gene isolated by the present invention is located at one of the quantitative trait loci (QTL) that were detected by utilizing the crossed progeny of "Habataki" and "Koshihikari", and was found to be located on chromosome 1. When the nucleotide sequence of this CKX gene was determined in Habataki and Koshihikari, differences in the nucleotides were found, and the CKX protein of Habataki, which has a larger particle-bearing number as compared to other varieties such as Koshihikari, was found to have lost its function.

Cytokinin (a general term for a group of compounds having biological activity similar to that of kinetin, and which have a substituent at position 6 of adenine), which is a phytohormone, is involved in promoting cell division, flower bud formation, lateral bud formation, suppression of aging, stomatal movement, root elongation, and such. In particular, promotion of flower bud formation and lateral bud formation may be closely linked to the trait of interest (increase in the number of glumous flowers). Using mevalonic acid as the substrate, cytokinin is synthesized via four catalytic reactions, but it is inactivated by cleavage at position 6 of adenine by cytokinin oxidase (for example, zeatin is degraded into adenine and methylbutenal). More specifically, when the function of the CKX (cytokinin oxidase) gene is lost, cytokinin cannot be degraded, and as a result, cytokinin accumulates. Since accumulation of cytokinin induces flower bud formation, this may lead to an increase in the particle-bearing number (number of glumous flowers), which agrees well with the function and phenotype of the CKX gene. This indicates that deletion of the function of the CKX gene increases the particle-bearing number (number of glumous flowers) of rice plants, and, as a result, the yield is increased. So far, a gene considered to be linked to the increase in particle-bearing number (number of glumous flowers) has neither been identified nor isolated. By proceeding through complicated steps, the present inventors finally elucidated the region where it exists and succeeded in isolating the gene as a single gene for the first time.

At present, increasing the particle-bearing number is an important breeding objective in Japanese rice variety improvement. Increasing the particle-bearing number directly leads to a trait that increases the grain yield, and since such traits are agriculturally very important, they are expected to be applied to breeding through the use of the CKX gene.

Since deletion of the function of the CKX gene increases the particle-bearing number of the plant, regulating the expression of this DNA using the antisense method, ribozyme method, and such can result in increasing the yield of grains. For example, by introducing the CKX gene in the antisense direction to a variety whose CKX gene is functioning, such as "Koshihikari", the particle-bearing number can be increased. Furthermore, the particle-bearing number can be increased by introducing an inactivated form of the CKX gene using molecular markers. The method of introduction may be transformation or crossing. The period of time required for transformation is very short as compared to gene transfer by crossing, and this allows the particle-bearing number to be increased without accompanying changes in other traits. The use of the CKX gene, which was isolated in this invention and relates to the increase and decrease of particle-bearing number, allows the particle-bearing number of rice plants to be changed easily, and may contribute to the cultivation of rice varieties whose particle-bearing number is increased. Since genomic synteny (genetic homology) is very highly conserved among grains, application of the rice CKX gene in breeding grains such as wheat, barley, and corn can be expected. Furthermore, since the CKX gene is not limited to grains and is widely distributed among plants, deletion of the CKX gene function may increase the number of flowers and seeds (glumous flowers) in all plants, leading to increased yield.

DNA encoding the CKX protein of the present invention include genomic DNA, cDNA, and chemically synthesized DNA. A genomic DNA and cDNA can be prepared according to conventional methods known to those skilled in the art. More specifically, a genomic DNA can be prepared, for example, as follows: (1) extract genomic DNA from rice varieties having the CKX gene (e.g. Koshihikari); (2) construct a genomic library (utilizing a vector, such as plasmid, phage, cosmid, BAC, and PAC); (3) spread the library; and (4) conduct colony hybridization or plaque hybridization using a probe prepared based on the DNA encoding a protein of the present invention (e.g. SEQ ID NO: 1 or 2). Alternatively, a genomic DNA can be prepared by PCR, using primers specific to a DNA encoding the protein of s present invention (e.g. SEQ ID NO: 1 or 2). On the other hand, cDNA can be prepared, for example, as follows: (1) synthesize cDNAs based on mRNAs extracted from rice varieties having the CKX gene (e.g. Koshihikari); (2) prepare a cDNA library by inserting the synthesized cDNA into vectors, such as λZAP; (3) spread the cDNA library; and (4) conduct colony hybridization or plaque hybridization as described above. Alternatively, cDNA can be also prepared by PCR.

The present invention includes DNAs encoding proteins (Koshihikari) functionally equivalent to the CKX protein of SEQ ID NO: 3. Herein, the term "functionally equivalent to the CKX protein" indicates that deletion of function of the object protein results in an increase in the particle-bearing number. Such DNA is derived preferably from monocotyledonous plants, more preferably from Gramineae, and most preferably from rice.

Examples of such DNAs include those encoding mutants, derivatives, alleles, variants, and homologues comprising the amino acid sequence of SEQ ID NO: 3 wherein one or more amino acids are substituted, deleted, added and/or inserted.

Examples of methods for preparing a DNA encoding a protein comprising altered amino acids well known to those skilled in the art include the site-directed mutagenesis (Kramer, W. and Fritz, H. -J., (1987) "Oligonucleotide-directed construction of mutagenesis via gapped duplex DNA." Methods in Enzymology, 154: 350-367). The amino acid sequence of a protein may also be mutated in nature due to the mutation of a nucleotide sequence. A DNA encoding proteins having the amino acid sequence of a natural CKX protein wherein one or more amino acids are substituted, deleted, and/or added are also included in the DNA of the present invention, so long as they encode a protein functionally equivalent to the natural CKX protein (SEQ ID NO: 3). Additionally, nucleotide sequence mutants that do not give rise to amino acid sequence changes in the protein (degeneracy mutants) are also included in the DNA of the present invention.

A DNA encoding a protein functionally equivalent to the CKX protein described in SEQ ID NO: 3 can be produced, for example, by methods well known to those skilled in the art including: methods using hybridization techniques (Southern, E. M.: Journal of Molecular Biology, Vol. 98, 503, 1975.); and polymerase chain reaction (PCR) techniques (Saiki, R. K. et al. Science, vol. 230, 1350-1354, 1985; Saiki, R. K. et al. Science, vol. 239, 487-491, 1988). That is, it is routine for a person skilled in the art to isolate a DNA with high homology to the CKX gene from rice and other plants using the nucleotide sequence of the CKX gene (SEQ ID NO: 2) or parts thereof as a probe, and oligonucleotides hybridizing specifically to the nucleotide sequence of CKX gene (SEQ ID NO: 2) as a primer. Such DNA encoding proteins functionally equivalent to the CKX protein, obtainable by hybridization techniques or PCR techniques, are included in the DNA of this invention.

Hybridization reactions to isolate such DNAs are preferably conducted under stringent conditions. Stringent hybridization conditions of the present invention include conditions such as: 6 M urea, 0.4% SDS, and 0.5× SSC; and those which yield a similar stringency to the conditions. DNAs with higher homology are expected when hybridization is performed under conditions with higher stringency, for example, 6 M urea, 0.4% SDS, and 0.1× SSC. Those DNAs isolated under such conditions are expected to encode a protein having a high amino acid level homology with CKX protein (SEQ ID NO: 3 or 6). Herein, high homology means an identity of at least 50% or more, more preferably 70% or more, and much more preferably 90% or more (e.g. 95%, 96%, 97%, 98%, 99%, or more), through the entire amino acid sequence. The degree of homology of one amino acid sequence or nucleotide sequence to another can be determined by following the algorithm BLAST by Karlin and Altschul (Proc. Natl. Acad. Sci. USA 87:2264-2268, 1990; Proc. Natl. Acad. Sci. USA, 90: 5873, 1993). Programs such as BLASTN and BLASTX were developed based on the BLAST algorithm (Altschul S F, et al. J. Mol. Biol. 215: 403, 1990). To analyze a nucleotide sequences according to BLASTN, the parameters are set, for example, as score=100 and word length=12. On the other hand, parameters used for the analysis of amino acid sequences by the BLASTX include, for example, score=50 and word length=3. Default parameters of each program are used when using BLAST and Gapped BLAST program. Specific techniques for such analyses are known in the art.

Evaluation of whether a particular DNA encodes a protein relating to the increase and decrease of the particle-bearing number of a plant can be performed as follows. The most conventional method involves deleting the function of the DNA, then performing the cultivation, and investigating the particle-bearing number. More specifically, the method involves cultivating under conditions where the function of the DNA is maintained, and under conditions where the function of the DNA is deleted, and comparing the resulting particle-bearing numbers. If the particle-bearing numbers do not change or are nearly the same, the DNA is judged not to be involved in the increase and decrease of the particle-bearing number. When the DNA is involved in the increase and decrease of the particle-bearing number, the particle-bearing number is further increased, and this difference is considered to be the degree of increase or decrease of the particle-bearing number.

The DNA of the present invention can be used, for example, to prepare recombinant proteins, and to produce plant transformants having an altered particle-bearing number. A recombinant protein is usually prepared by inserting a DNA encoding a protein of the present invention into an appropriate expression vector, introducing the vector into an appropriate cell, culturing the transformed cells, allowing the cells to express the recombinant protein, and purifying the expressed protein. A recombinant protein can be expressed as a fusion protein with other proteins so as to be easily purified, for example, as a fusion protein with maltose binding protein in *Escherichia coli* (New England Biolabs, USA, vector pMAL series), as a fusion protein with glutathione-S-transferase (GST) (Amersham Pharmacia Biotech, vector pGEX series), or tagged with histidine (Novagen, pET series). The host cell is not limited so long as the cell is suitable for expressing the recombinant protein. It is possible to utilize yeasts or various animal, plant, or insect cells besides the above described *E. coli*. A vector can be introduced into a host cell by a variety of methods known to one skilled in the art. For example, a transformation method using calcium ions (Mandel, M. and Higa, A. (1970) Journal of Molecular Biology, 53, 158-162, Hanahan, D. (1983) Journal of Molecular Biology, 166, 557-580) can be used to introduce a vector into *E. coli*. A recombinant protein expressed in host cells can be purified and recovered from the host cells or the culture supernatant thereof by known methods. When a recombinant protein is expressed as a fusion protein with maltose binding protein or other partners, the recombinant protein can be easily purified by affinity chromatography. A protein of the present invention can be prepared from transformed plants which have been generated by introducing a DNA of this invention into plants as described below. Thus, the transformed plants of the present invention include not only the plants harboring a DNA of this invention which has been introduced to alter the particle-bearing number as described below, but also the plants harboring a DNA of this invention which has been introduced to prepare a protein of this invention.

The resulting protein can be used to prepare an antibody that binds to the protein. For example, a polyclonal antibody can be prepared by immunizing immune animals, such as rabbits, with a purified protein of the present invention or a portion thereof, collecting blood after a certain period, and removing clots. A monoclonal antibody can be prepared by fusing myeloma cells with the antibody-forming cells of animals immunized with the above protein or its portion, isolating a monoclonal cell expressing a desired antibody (hybridoma), and recovering the antibody from the cell. The obtained antibody can be utilized to purify or detect a protein of the present invention. Accordingly, the present invention includes antibodies that bind to proteins of the invention. The use of these antibodies enables one to distinguish the expression site of proteins involved in the increase and decrease of the particle-bearing number of a plant body, or determine whether the plant species express the protein involved in the increase and decrease of the particle-bearing number.

For example, since an antibody that specifically recognizes the amino acid sequence of the carboxyl terminus of "Koshihikari" having a small particle-bearing number does not bind to proteins expressed in varieties such as "Habataki" having a large particle-bearing number, it can be used to distinguish whether or not the protein involved in the increase and decrease of particle-bearing number is expressed in a particular plant species.

When producing a transformed plant in which the particle-bearing number has been increased by utilizing the DNA of this invention, a DNA for suppressing the expression of the DNA encoding the protein of this invention is inserted into an appropriate vector, which is then introduced into a plant cell. The transformed plant cells obtained by these steps are then regenerated. The plant cells to receive the vector are preferably plant cells that show normal expression of the DNA of this invention. "Suppressing the expression of the DNA encoding the protein of this invention" includes suppression of gene transcription and suppression of translation into the protein. Furthermore, it not only includes complete termination of DNA expression, but also includes decreased expression.

Suppression of the expression of a particular endogenous gene in a plant can be performed, for example by utilizing a DNA that encodes an RNA complementary to the transcript of the DNA encoding the protein of this invention.

One embodiment of "a DNA that encodes an RNA complementary to the transcript of the DNA encoding the protein of this invention" is a DNA that encodes an antisense RNA complementary to the transcript of the DNA encoding the protein of this invention. Ecker et al. were the first to demonstrate the antisense effect of an antisense RNA introduced by electroporation in plant cells by using the transient gene expression method (J. R. Ecker and R. W. Davis (1986) Proc. Natl. Acad. Sci. USA 83: 5372). Thereafter, the target gene expression was reportedly reduced in tobacco and petunias by expressing antisense RNAs (A. R. van der Krol et al. (1988)

Nature 333: 866). The antisense technique has now been established as a means to repress target gene expression in plants.

Multiple factors cause antisense nucleic acids to repress the target gene expression. These include: inhibition of transcription initiation by triple strand formation; repression of transcription by hybrid formation at the site where the RNA polymerase has formed a local open loop structure; transcription inhibition by hybrid formation with the RNA being synthesized; repression of splicing by hybrid formation at the junction between an intron and an exon; repression of splicing by hybrid formation at the site of spliceosome formation; repression of mRNA translocation from the nucleus to the cytoplasm by hybrid formation with mRNA; repression of splicing by hybrid formation at the capping site or at the poly A addition site; repression of translation initiation by hybrid formation at the binding site for the translation initiation factors; repression of translation by hybrid formation at the site for ribosome binding near the initiation codon; inhibition of peptide chain elongation by hybrid formation in the translated region or at the polysome binding sites of mRNA; and repression of gene expression by hybrid formation at the sites of interaction between nucleic acids and proteins. These factors repress the target gene expression by inhibiting the process of transcription, splicing, or translation (Hirashima and Inoue, "Shin Seikagaku Jikken Koza (New Biochemistry Experimentation Lectures) 2, Kakusan (Nucleic Acids) IV, Idenshi No Fukusei To Hatsugen (Replication and Expression of Genes)," Nihon Seikagakukai Hen (The Japanese Biochemical Society), Tokyo Kagaku Dozin, pp. 319-347, (1993)).

An antisense sequence of the present invention can repress the target gene expression by any of the above mechanisms. In one embodiment, if an antisense sequence is designed to be complementary to the untranslated region near the 5' end of the gene's mRNA, it will effectively inhibit translation of a gene. It is also possible to use sequences complementary to the coding regions or to the untranslated region on the 3' side. Thus, the antisense DNA used in the present invention include DNA having antisense sequences against both the untranslated regions and the translated regions of the gene. The antisense DNA to be used is connected downstream from an appropriate promoter, and, preferably, a sequence containing the transcription termination signal is connected on the 3' side. The DNA thus prepared can be transfected into the desired plant by known methods. The sequence of the antisense DNA is preferably a sequence complementary to the endogenous gene of the plant to be transformed or a part thereof, but it need not be perfectly complementary, so long as it can effectively inhibit the gene expression. The transcribed RNA is preferably at least 90%, and most preferably at least 95% complementary to the transcripts of the target gene. In order to effectively inhibit the expression of the target gene by means of an antisense sequence, the antisense DNA should be at least 15 nucleotides long, more preferably at least 100 nucleotides long, and still more preferably at least 500 nucleotides long. The antisense DNA to be used is generally shorter than 5 kb, and preferably shorter than 2.5 kb.

DNA encoding ribozymes can also be used to repress the expression of endogenous genes. A ribozyme is an RNA molecule that has catalytic activity. There are many known ribozymes having various activities. Research on ribozymes as RNA cleaving enzymes has enabled the design of a ribozyme that site-specifically cleaves RNA. While some ribozymes of the group I intron type or the M1RNA contained in RNaseP consist of 400 nucleotides or more, others belonging to the hammerhead type or the hairpin type have an activity domain of about 40 nucleotides (Makoto Koizumi and Eiko Ohtsuka (1990) Tanpakushitsu Kakusan Kohso (Protein, Nucleic acid and Enzyme) 35: 2191).

The self-cleavage domain of a hammerhead type ribozyme cleaves at the 3' side of C15 of the sequence G13U14C15. Formation of a nucleotide pair between U14 and A at the ninth position is considered important for the ribozyme activity. Furthermore, it has been shown that the cleavage also occurs when the nucleotide at the 15th position is A or U instead of C (M. Koizumi et al. (1988) FEBS Lett. 228: 225). If the substrate binding site of the ribozyme is designed to be complementary to the RNA sequences adjacent to the target site, one can create a restriction-enzyme-like RNA cleaving ribozyme which recognizes the sequence UC, UU, or UA within the target RNA (M. Koizumi et al. (1988) FEBS Lett. 239: 285; Makoto Koizumi and Eiko Ohtsuka (1990) Tanpakushitsu Kakusan Kohso (Protein, Nucleic acid and Enzyme), 35: 2191; M. Koizumi et al. (1989) Nucleic Acids Res. 17: 7059). For example, in the coding region of the CKX gene (SEQ ID NO: 2), there are a number of sites that can be used as the ribozyme target.

The hairpin type ribozyme is also useful in the present invention. A hairpin type ribozyme can be found, for example, in the minus strand of the satellite RNA of the tobacco ringspot virus (J. M. Buzayan, Nature 323: 349 (1986)). This ribozyme has also been shown to target-specifically cleave RNA (Y. Kikuchi and N. Sasaki (1992) Nucleic Acids Res. 19: 6751; Yo Kikuchi (1992) Kagaku To Seibutsu (Chemistry and Biology) 30: 112).

The ribozyme designed to cleave the target is fused with a promoter, such as the cauliflower mosaic virus 35S promoter, and with a transcription termination sequence, so that it will be transcribed in plant cells. However, if extra sequences have been added to the 5' end or the 3' end of the transcribed RNA, the ribozyme activity can be lost. In this case, one can place an additional trimming ribozyme, which functions in cis to perform the trimming on the 5' or the 3' side of the ribozyme portion, in order to precisely cut the ribozyme portion from the transcribed RNA containing the ribozyme (K. Taira et al. (1990) Protein Eng. 3: 733; A. M. Dzaianott and J. J. Bujarski (1989) Proc. Natl. Acad. Sci. USA 86: 4823; C. A. Grosshands and R. T. Cech (1991) Nucleic Acids Res. 19: 3875; K. Taira et al. (1991) Nucleic Acid Res. 19: 5125). Multiple sites within the target gene can be cleaved by arranging these structural units in tandem to achieve greater effects (N. Yuyama et al., Biochem. Biophys. Res. Commun. 186: 1271 (1992)). By using such ribozymes, it is possible to specifically cleave the transcripts of the target gene in the present invention, thereby repressing the expression of the gene.

Another embodiment of "a DNA that encodes an RNA complementary to the transcript of the DNA encoding the protein of this invention" is a DNA encoding a dsRNA complementary to the transcript of the DNA encoding the protein of this invention. RNAi is a phenomenon where introduction into cells of a double-stranded RNA (hereinafter, dsRNA) comprising a sequence identical or similar to a target genetic sequence suppresses the expression of both the introduced foreign gene and the endogenous target gene. When approximately 40 to several hundred base pairs of dsRNA are introduced into cells, an RNaseIII-like nuclease called Dicer, which has a helicase domain, excises the dsRNA in the presence of ATP from the 3' end, approximately 21 to 23 base pairs at a time, and produces siRNA (short interference RNA). Binding of a specific protein to this siRNA forms a nuclease complex (RISC: RNA-induced silencing complex). This complex recognizes and binds a sequence that is the same as that of siRNA, and cleaves the mRNA of the target gene at a location corresponding to the center of siRNA by RNaseIII-like enzyme activity. Besides this pathway, the antisense strand of siRNA binds to mRNA and acts as a primer for RNA-dependent RNA polymerase (RsRP) to synthesize dsRNA. One may also consider a pathway in which this dsRNA becomes the substrate of Dicer again, to produce a new siRNA to amplify its action.

The above-mentioned RNAi was initially found in *Caenorhabditis elegans* (Fire, A. et al. Potent and specific genetic interference by double-stranded RNA in *Caenorhabditis elegans*. Nature 391, 806-811, (1998)) and has now been observed not only in *C. elegans* but also in various organisms such as plants, nematodes, fruit flies, and protozoans (Fire, A. RNA-triggered gene silencing. Trends Genet. 15, 358-363 (1999); Sharp, P. A. RNA interference 2001. Genes Dev. 15, 485-490 (2001); Hammond, S. M., Caudy, A. A. & Hannon, G. J. Post-transcriptional gene silencing by double-stranded RNA. Nature Rev. Genet. 2, 110-1119 (2001); Zamore, P. D. RNA interference: listening to the sound of silence. Nat. Struct. Biol. 8, 746-750 (2001)). The actual introduction of dsRNA from the outside confirmed that expression of the target gene can be suppressed in these organisms, and this is also being utilized as a method for producing knockout individuals.

Initially when RNAi was introduced, the notion was that dsRNA had to be of a certain length (40 nucleotides) or longer for it to be effective. However, Tuschl et al. (Rockefeller University, U.S.A.) reported that by introducing 21 base pairs or so of short chain dsRNA (siRNA) into cells, the RNAi effect was observed, even in mammalian cells, without causing antiviral response due to PKR (Tuschl, Nature, 411, 494-498 (2001)), and RNAi suddenly received attention as a technique applicable to differentiated mammalian cells such as that of humans.

The DNA of this invention comprises an antisense-encoding DNA that encodes an antisense RNA against any one of the regions of the target gene mRNA, and a sense-encoding DNA that encodes a sense RNA of any one of the regions of the target gene mRNA, and the antisense RNA and the sense RNA can be expressed from the antisense-encoding DNA and the sense-encoding DNA. dsRNA can also be prepared from these antisense RNA and sense RNA.

When the dsRNA expression system of this invention is incorporated into a vector or the like, the antisense RNA and sense RNA may be expressed from the same vector, or they may be expressed from different vectors. For example, antisense RNA and sense RNA can be expressed from the same vector by individually assembling an antisense RNA expression cassette and sense RNA expression cassette in which a promoter that may express a short RNA, such as the polIII system, is linked upstream of the antisense-encoding DNA and sense-encoding DNA, respectively, and inserting these cassettes into a vector in the same direction or in reverse direction. Furthermore, an expression system that has the antisense-encoding DNA and sense-encoding DNA positioned in opposite directions so that they face each other on different strands can be composed. In this arrangement, a single double-stranded DNA in which the antisense RNA-encoding strand and sense RNA-encoding strand are paired (siRNA-encoding DNA) is provided, and promoters can be furnished on both sides in opposite directions so that antisense RNA and sense RNA can be expressed from each of the strands. In this case, to avoid addition of an unnecessary sequence downstream of the sense RNA or antisense RNA, a terminator is preferably placed at the 3' end of each of the strands (antisense RNA-encoding strand and sense RNA-encoding strand). A sequence of four or more continuous A (adenine) nucleotides can be used as this terminator. Furthermore, in this palindromic expression system, the types of the two promoters are preferably different.

On the other hand, antisense RNA and sense RNA can be expressed from different vectors by, for example, individually assembling an antisense RNA expression cassette and sense RNA expression cassette in which a promoter that may initiate expression of a short RNA, such as the polIII system, is linked upstream of the antisense-encoding DNA and sense-encoding DNA, respectively, and inserting these cassettes into different vectors.

In the RNAi of this invention, siRNA may be used as the dsRNA. The term "siRNA" refers to a double-stranded RNA comprising short chains in a range that does not indicate toxicity within cells, and is not limited to an overall length of 21 to 23 base pairs as reported by Tuschl et al. (supra), so long as the length is within the range that does not indicate toxicity. For example, the length may be 15 to 49 base pairs, preferably 15 to 35 base pairs, and more preferably 21 to 30 base pairs. Alternatively, the siRNA to be expressed may be transcribed such that the final length of the double-stranded RNA portion may be, for example, 15 to 49 base pairs, preferably 15 to 35 base pairs, and more preferably 21 to 30 base pairs.

A construct that forms a double-stranded RNA having a hairpin structure (self-complementary 'hairpin' RNA (hpRNA)) upon insertion of an appropriate sequence (preferably an intron sequence) between the inverted repeats of the target sequence (Smith, N. A. et al. Nature, 407:319, 2000; Wesley, S. V. et al. Plant J. 27:581, 2001; Piccin, A. et al. Nucleic Acids Res. 29:E55, 2001), may also be used as the DNA of this invention.

The DNA used for RNAi does not have to be completely identical to the target gene, but should have a sequence identity of at least 70% or more, preferably 80% or more, more preferably 90% or more, and most preferably 95% or more. The sequence identity can be determined by the methods described above.

In dsRNA, the double-stranded portion in which the RNAs are paired is not limited to those that are completely paired, and it may include unpaired portions caused by mismatches (wherein the corresponding nucleotides are not complementary), bulges (wherein one of the strands lacks corresponding nucleotides), and such. In the present invention, the double-stranded RNA region in which the RNAs of dsRNA are paired may include both bulges and mismatches.

Endogenous gene expression can also be repressed by cosuppression through the transformation by DNA having a sequence identical or similar to the target gene sequence. "Cosuppression" refers to the phenomenon whereby a gene having a sequence identical or similar to the target endogenous gene sequence is introduced into plants by transformation and expression of both the introduced exogenous gene and the target endogenous gene becomes repressed. Although the detailed mechanism of cosuppression is unknown, it is frequently observed in plants (Curr. Biol. 7: R793, 1997, Curr. Biol. 6: 810, 1996). For example, if one wishes to obtain a plant body in which the CKX gene is cosuppressed, the plant in question can be transformed with a vector DNA designed so as to express the CKX gene or a DNA having a similar sequence to select a plant having the CKX mutant character, i.e., a plant with reduced photoperiod sensitivity, among the resultant plants. The gene to be used for cosuppression does not need to be completely identical to the target gene, but it should have at least 70% or more sequence identity, preferably 80% or more sequence identity, and more preferably 90% or more (e.g. 95%, 96%, 97%, 98%, 99%, or more) sequence identity.

In addition, endogenous gene expression in the present invention can also be repressed by transforming the plant with a gene having the dominant negative phenotype of the target gene. Herein, a gene having the dominant negative phenotype refers to a gene which, when expressed, can eliminate or reduce the activity of the wild type endogenous gene inherent to the plant.

The present invention provides vectors into which the DNA of this invention or a DNA that suppresses the expression of the DNA of this invention has been inserted. In addition to the above-mentioned vectors used to produce recombinant proteins, the vectors of this invention also include vectors for expressing the DNA of this invention or a DNA that suppresses the expression of the DNA of this invention in plant cells in order to produce transformed plants. There are no limitations on the type of vectors used, so long as they contain a promoter sequence that can initiate transcription in plant cells, and a terminator sequence comprising a polyadenylation site required for stabilization of the transcript. Examples include plasmids "pBI121", "pBI221", and "pBI101" (all from Clontech). The vectors used for transformation of plant cells are not particularly limited so long as they can express the inserted gene within the cells. For example, vectors comprising a promoter for performing a constitutive gene expression in plant cells (for example, the 35S promoter of cauliflower mosaic virus), and vectors comprising a promoter that is inductively activated by external stimulus may be used. The term "plant cells" used herein includes various forms of plant cells such as suspension culture cells, protoplasts, leaf sections, and calli.

The vector of this invention may comprise a promoter for constitutively or inductively expressing the protein of this invention. Examples of promoters for constitutive expression include the 35S promoter of cauliflower mosaic virus (Odell et al. 1985 Nature 313:810), actin promoter of rice (Zhang et al. 1991 Plant Cell 3:1155), and ubiquitin promoter of corn (Cornejo et al. 1993 Plant Mol. Biol. 23:567).

Examples of promoters for inductive expression include promoters known to initiate expression due to extrinsic factors, such as infection and invasion of filamentous fungi, bacteria, and viruses, low temperature, high temperature, dryness, ultraviolet irradiation, and spraying of particular compounds. Examples of such promoters include the chitinase gene promoter of rice (Xu et al. 1996 Plant Mol. Biol. 30:387) and the tobacco PR protein gene promoter (Ohshima et al. 1990 Plant Cell 2:95), which are induced by infection and invasion of filamentous fungi, bacteria, and viruses, the "lip19" gene promoter of rice induced by low temperature (Aguan et al. 1993 Mol. Gen Genet. 240:1), the "hsp 80" gene and "hsp 72" gene promoters of rice induced by high temperature (Van Breusegem et al. 1994 Planta 193:57), the "rab 16" gene promoter of *Arabidopsis thaliana* induced by dryness (Nundy et al., 1990 Proc. Natl. Acad. Sci. USA 87:1406), chalcone synthase gene promoter of parsley induced by ultraviolet irradiation (Schulze-Lefert et al. 1989 EMBO J. 8:651), and the alcohol dehydrogenase gene promoter of corn induced by anaerobic conditions (Walker et al., 1987 Proc. Natl. Acad. Sci. USA 84:6624). In addition, the chitinase gene promoter of rice and PR protein gene promoter of tobacco can also be induced by specific compounds such as salicylic acid, and the "rab 16" can also be induced by the spraying of abscisic acid, a phytohormone.

Furthermore, the present invention provides transformed cells to which a vector of this invention has been introduced. The cells to which a vector of this invention is introduced include, in addition to the above-mentioned cells used for producing recombinant proteins, plant cells for preparing transformed plants. There are no particular limitations on the type of plant cells, and examples are cells of *Arabidopsis thaliana*, rice, corn, potato, and tobacco. The plant cells of this invention include, in addition to cultured cells, cells within the plant, and also protoplasts, shoot primordia, multiple shoots, and hairy roots. A vector can be introduced into plant cells by known methods, such as the polyethylene glycol method, electroporation, *Agrobacterium* mediated transfer, and particle bombardment. Plants can be regenerated from transformed plant cells by known methods depending on the type of the plant cell (Toki et al., (1995) Plant Physiol. 100:1503-1507). For example, transformation and regeneration methods for rice plants include: (1) introducing genes into protoplasts using polyethylene glycol, and regenerating the plant body (suitable for indica rice varieties) (Datta, S. K. (1995) in "Gene Transfer To Plants", Potrykus I and Spangenberg Eds., pp 66-74); (2) introducing genes into protoplasts using electric pulse, and regenerating the plant body (suitable for japonica rice varieties)(Toki et al. (1992) Plant Physiol. 100, 1503-1507); (3) introducing genes directly into cells by the particle bombardment, and regenerating the plant body (Christou et al. (1991) Bio/Technology, 9: 957-962); and (4) introducing genes using *Agrobacterium*, and regenerating the plant body (Hiei et al. (1994) Plant J. 6: 271-282). These methods are already established in the art and are widely used in the technical field of the present invention. Such methods can be suitably used for the present invention.

Plants can be regenerated by redifferentiating transformed plant cells. Methods of redifferentiation differ depending on the type of plant cells, and examples include the method of Fujimura et al. (Plant Tissue Culture Lett. 2:74 (1995)) for rice, the methods of Shillito et al. (Bio/Technology 7:581 (1989)) and Gorden-Kamm et al. (Plant Cell 2:603 (1990)) for corn, the method of Visser et al. (Theor. Appl. Genet. 78:594 (1989)) for potato, the method of Nagata and Takebe (Planta 99:12 (1971)) for tobacco, the method of Akama et al. (Plant Cell Reports 12:7-11 (1992)) for *Arabidopsis thaliana*, and the method of Dohi et al. (Unexamined Published Japanese Patent Application No. (JP-A) Hei 8-89113) for eucalyptus.

Once a transformed plant to which the DNA of the present invention or a DNA that suppresses the expression of the DNA of the present invention has been integrated into its genome is obtained, it is possible to obtain a progeny of the plant by sexual or asexual reproduction. It is also possible to obtain reproductive material (such as seeds, fruits, spikes, tubers, tuberous roots, stubs, calli, and protoplasts) from the plant or a progeny or clone thereof, to mass-produce the plant based on such material. Thus, the present invention includes plant cells to which the DNA of the present invention has been introduced, plants containing these cells, progenies and clones of these plants, as well as reproductive material of the plants, and their progenies and clones.

Plants produced in this manner and whose particle-bearing number has been modified show changes in their particle-bearing number and yield when compared to the wild-type plants. For example, plants in which expression of DNA encoding the CKX protein has been suppressed by the introduction of an antisense DNA and such are expected to show increase in yield due to increase in their particle-bearing number. Use of the method of this invention, can increase the particle-bearing number of rice, which is a useful agricultural crop. The present invention is further beneficial in the development of high-yielding rice varieties.

Furthermore, the present invention provides polynucleotides comprising at least 15 continuous nucleotides, which are complementary to the nucleotide sequence of SEQ ID NO: 1 or 2, or their complementary sequences. Herein, the phrase "complementary sequence" refers to a sequence of the other strand with respect to the sequence of one of the strands of a double-stranded DNA comprising A:T and G:C base pairs. The term "complementary" is not limited to the case in which a sequence is completely complementary in the region of at least 15 continuous nucleotides, and includes cases in which the nucleotide sequence identity is at least 70%, preferably at least 80%, more preferably 90%, and even more preferably 95% or more. Such DNAs are useful as probes for performing detection or isolation of the DNAs of this invention, and as primers for amplifying the DNAs.

Furthermore, the present invention provides methods of genetic diagnosis for determining the increase and decrease in the particle-bearing number of a plant. The particle-bearing number of a plant is closely related to the yield of the plant, and determining the particle-bearing number of a plant is very important in breeding rice varieties for the purpose of increasing the yield.

In the present invention, the phrase "determining the increase and decrease of the particle-bearing number of a plant" includes not only determining the increase and decrease in the particle-bearing number of the varieties cultivated so far, but also includes determining the increase and decrease of the particle-bearing number of new varieties produced by crossing or genetic recombination techniques.

The method of evaluating the increase and decrease of the particle-bearing number of a plant of this invention is characterized by detecting whether or not the plant has lost the function of the DNA encoding the CKX protein. Whether or not the plant has lost the function of the DNA encoding the CKX protein can be evaluated by detecting the change in the nucleotide sequence of genomic DNA corresponding to the CKX gene.

After the nucleotide sequence of a region of a test plant DNA corresponding to the DNA of this invention is determined directly, the plant is determined to be a variety having a small particle-bearing number when the nucleotide sequence encodes a protein whose deletion of function causes an increase in the particle-bearing number of a plant, or determined to be a variety having a large particle-bearing number when this protein is not encoded.

For example, if a mutation causing a deletion of the function of the rice CKX protein is found in the nucleotide sequence of a test plant DNA, this test plant will be diagnosed as a variety having a large particle-bearing number.

Evaluation of the increase and decrease of the particle-bearing number of a plant by the method of this invention has advantages, for example, when breeding improved varieties by crossing plants. For example, when introduction of a trait that increases the particle-bearing number is not desired, one can avoid crossing with varieties having the trait of increasing the particle-bearing number, and in reverse, when introduction of a trait that increases the particle-bearing number is desired, crossing can be performed with varieties having the trait of increasing the particle-bearing number. It is further effective when selecting desirable individuals from crossed progenies. Determination of the increase and decrease of the particle-bearing number of plants at the genetic level can be performed more conveniently and reliably compared to determination from the phenotype. Therefore, the method for evaluating the increase and decrease of particle-bearing number of this invention may greatly contribute to the breeding of improved plant varieties.

BRIEF DESCRIPTION OF THE DRAWINGS

FIG. 8 is the continuation of FIG. 7.

FIG. 9 is the continuation of FIG. 8.

BEST MODE FOR CARRYING OUT THE INVENTION

Hereinafter, the present invention is specifically illustrated with reference to Examples, but is not to be construed as being limited thereto.

EXAMPLE 1

Selection of Test Materials and Production of a Semi-isogenic Line

Figure 1:
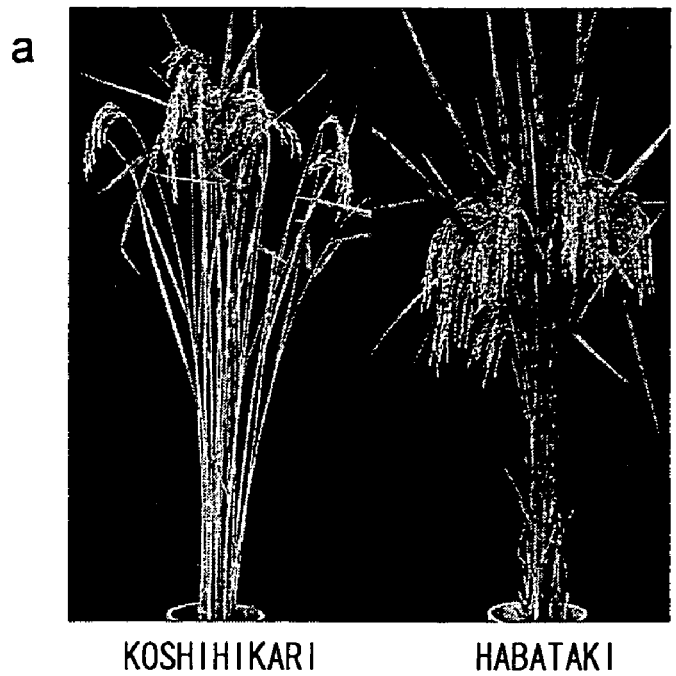
FIG. 1 shows a set of photographs that depict the phenotype of Koshihikari and Habataki. Koshihikari is shown on the left and Habataki is shown on the right.
Figure 1:
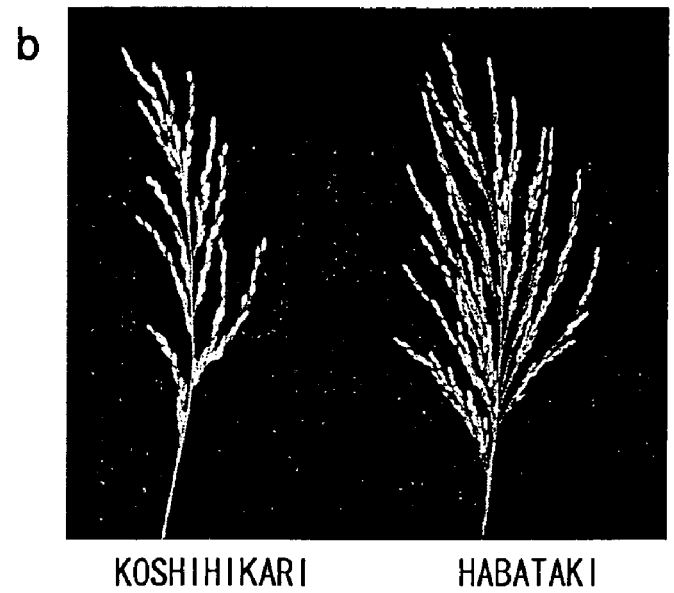

Initially, in order to generate a hybrid population for QTL analysis, varieties that would become the parents of the hybrids were selected. First, the average particle-bearing numbers in several varieties of japonica rice and several varieties of indica rice were investigated, and from these varieties, two varieties showing a clear difference in the particle-bearing number, "Koshihikari" which is a japonica rice, and "Habataki" which is an indica rice, were selected (FIG. 1). To F1 individuals produced by crossing japonica rice "Koshihikari" and indica rice "Habataki", backcrossing using Koshihikari as the repeated parent and self-fertilization were carried out, and 74 varieties of BC2F1, BC2F2, and BC3F2 population were cultivated and developed on the Nagoya University Farm.

Figure 2:
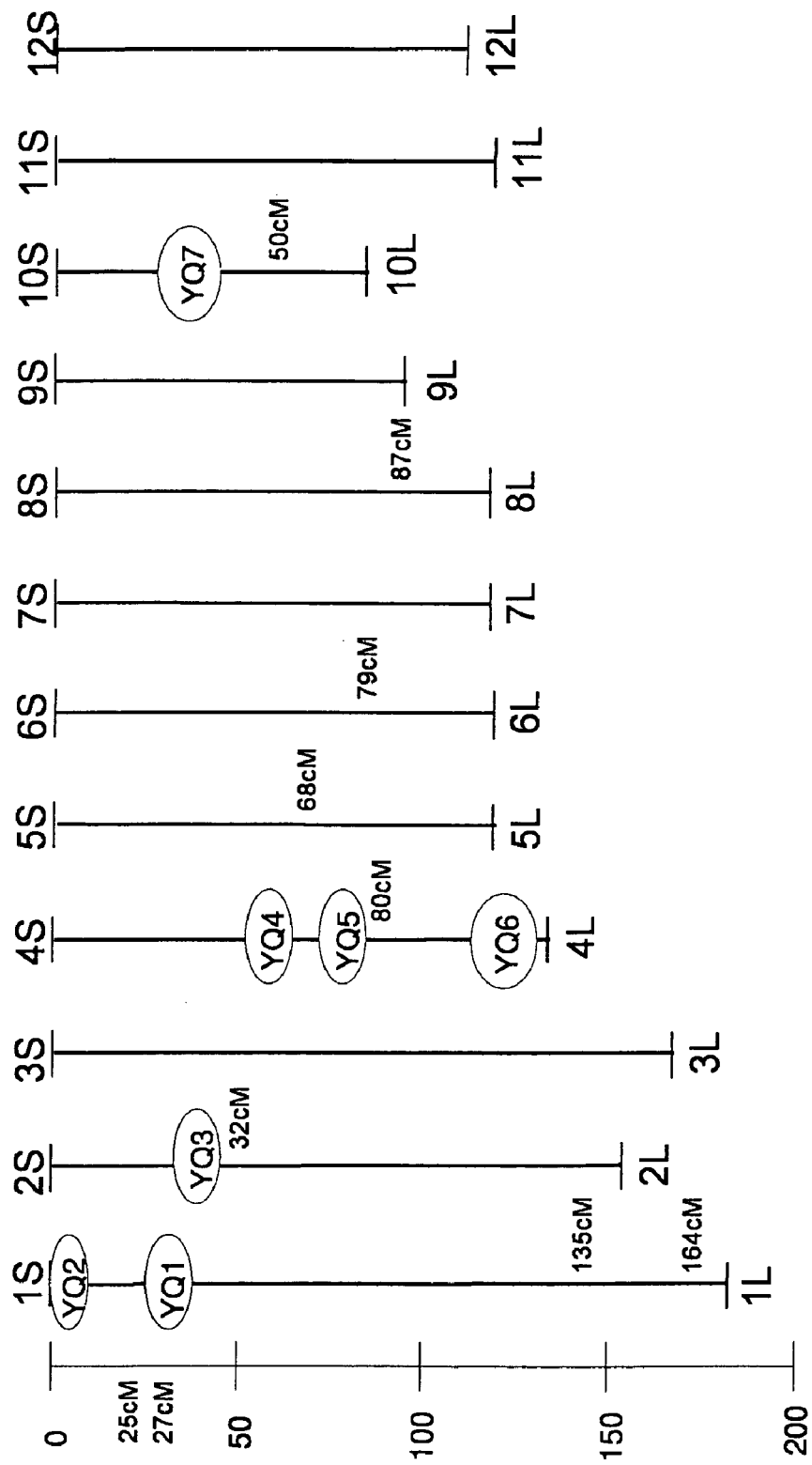
FIG. 2 shows the positions of Yielding QTL(YQ) on the chromosome.

By performing a QTL analysis relating to the particle-bearing number using 74 BC2F2 plants, a plurality of QTL that increase the particle-bearing number was detected (FIG. 2). In particular, a QTL (YQ1; Yielding QTL 1) of Habataki, located at approximately 28 cM in the short arm of chromosome 1 (FIG. 2), was successfully discovered to be very effective in increasing the grain (or seed) number as compared to that of Koshihikari. To verify the presence of YQ1, repeated backcrossing and MAS were used to produce a YQ1 semi-isogenic line (Nil-YQ1: a variety in which the locus of Habataki, the locus at approximately 28 cM in the short arm of chromosome 1, is substituted into the chromosome of Koshihikari). The maximum particle-bearing numbers of Nil-YQ1 and Koshihikari (control) were investigated, and as a result, the presence of QTL(YQ1) was confirmed. Varieties in which the locus at approximately 28 cM in the short arm of chromosome 1 was substituted with that of Habataki increased their particle-bearing number by 50 on average.

EXAMPLE 2

QTL Analysis

From each of the 74 BC2F1 individuals, DNAs were extracted using the CTAB method, and the genotype of each individual was determined using 93 molecular markers that thoroughly cover all chromosomes. Their self-fertilized progeny, BC2F2, was developed at ten individuals per variety, and from among them, one individual per variety was randomly selected, and after sampling six panicles from each of the selected individuals, the particle-bearing number was investigated for each panicle. Among the six panicles of each variety, the panicle having the largest particle-bearing number was selected, and this number was used as the maximum particle-bearing number. QTL analysis was performed using the Qgene software.

EXAMPLE 3

High Resolution Linkage Analysis Using a Segregating Population of YQ

Figure 3:
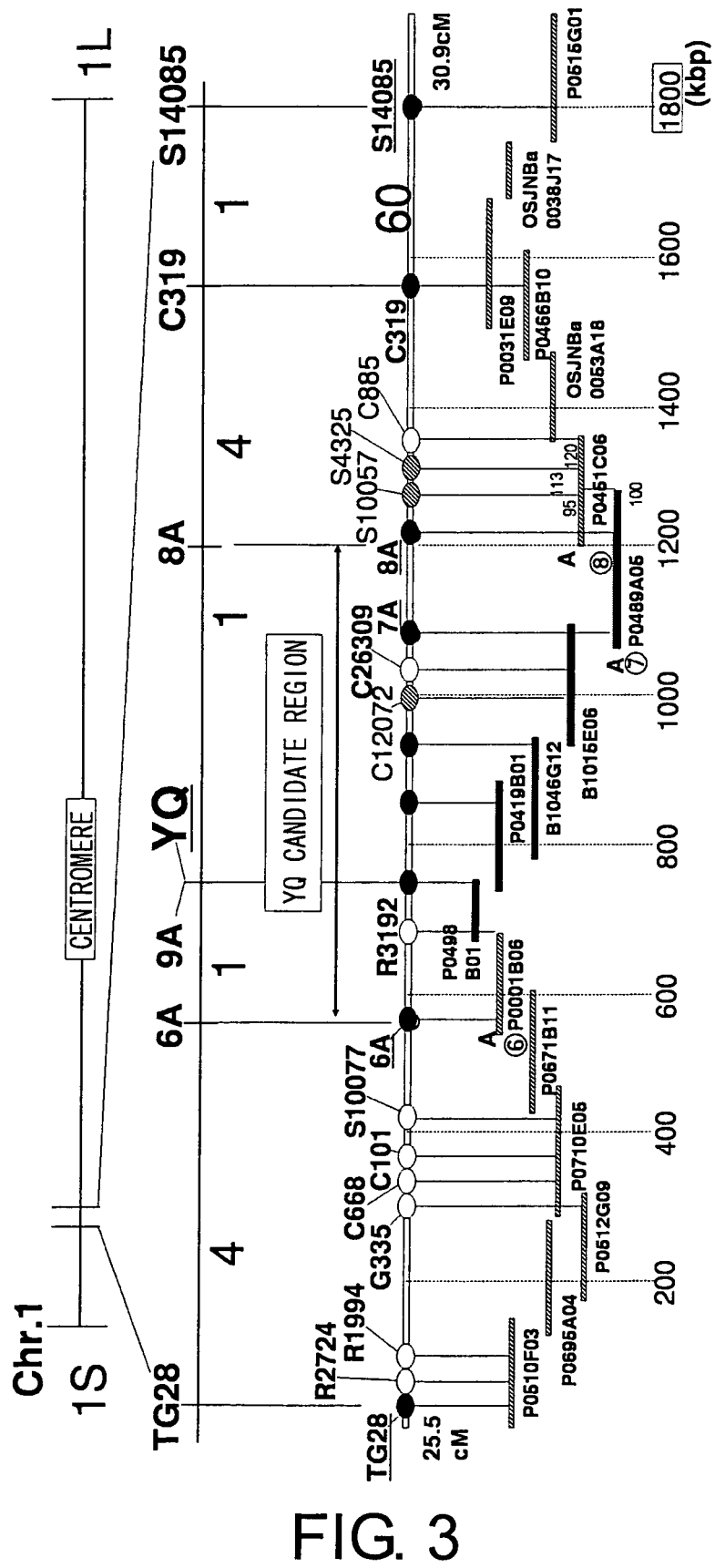
FIG. 3 shows a small scale linkage map of Yielding QTL (YQ).
Figure 4:
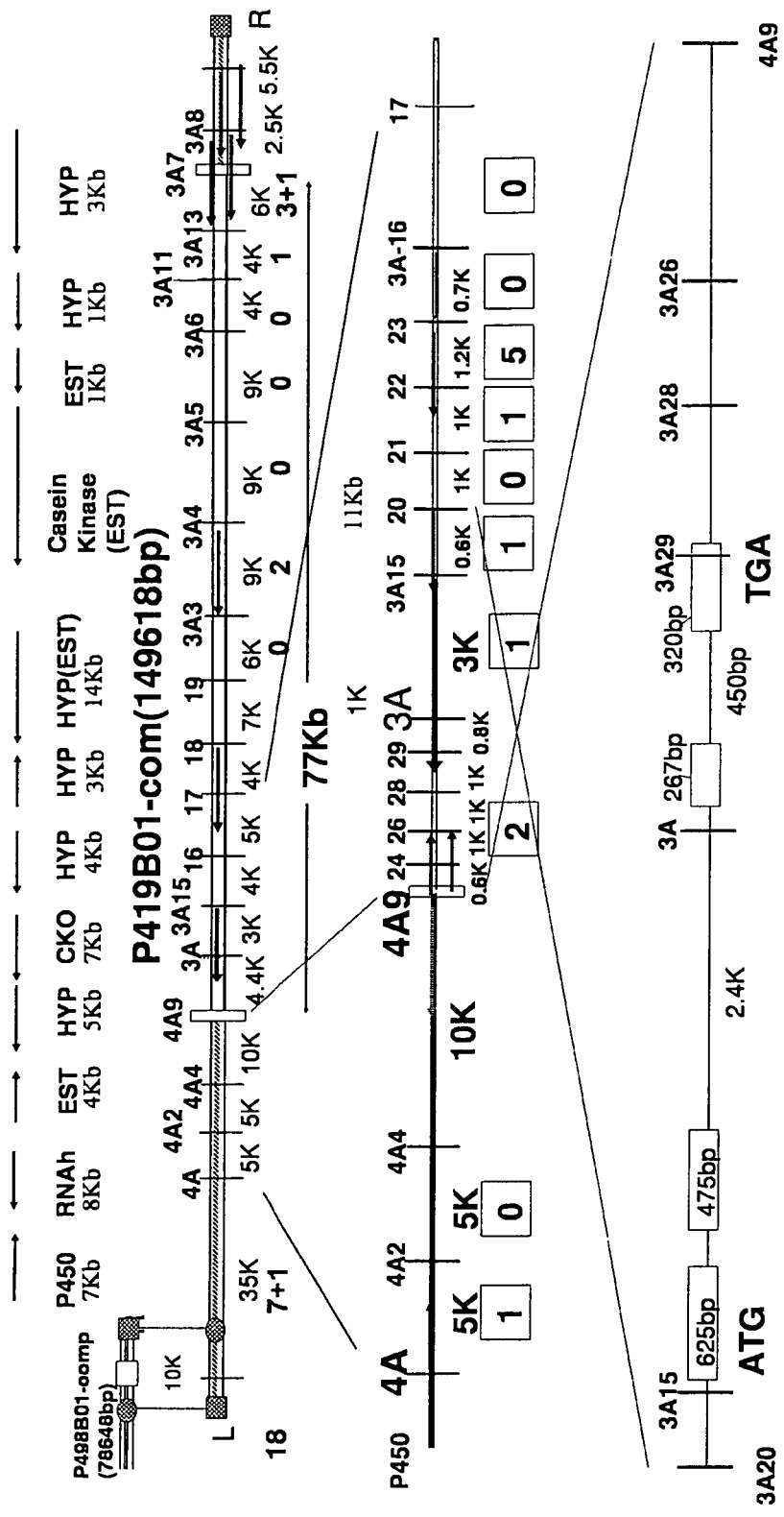
FIG. 4 shows a high-resolution linkage map of Yielding QTL(YQ).
Figure 5:
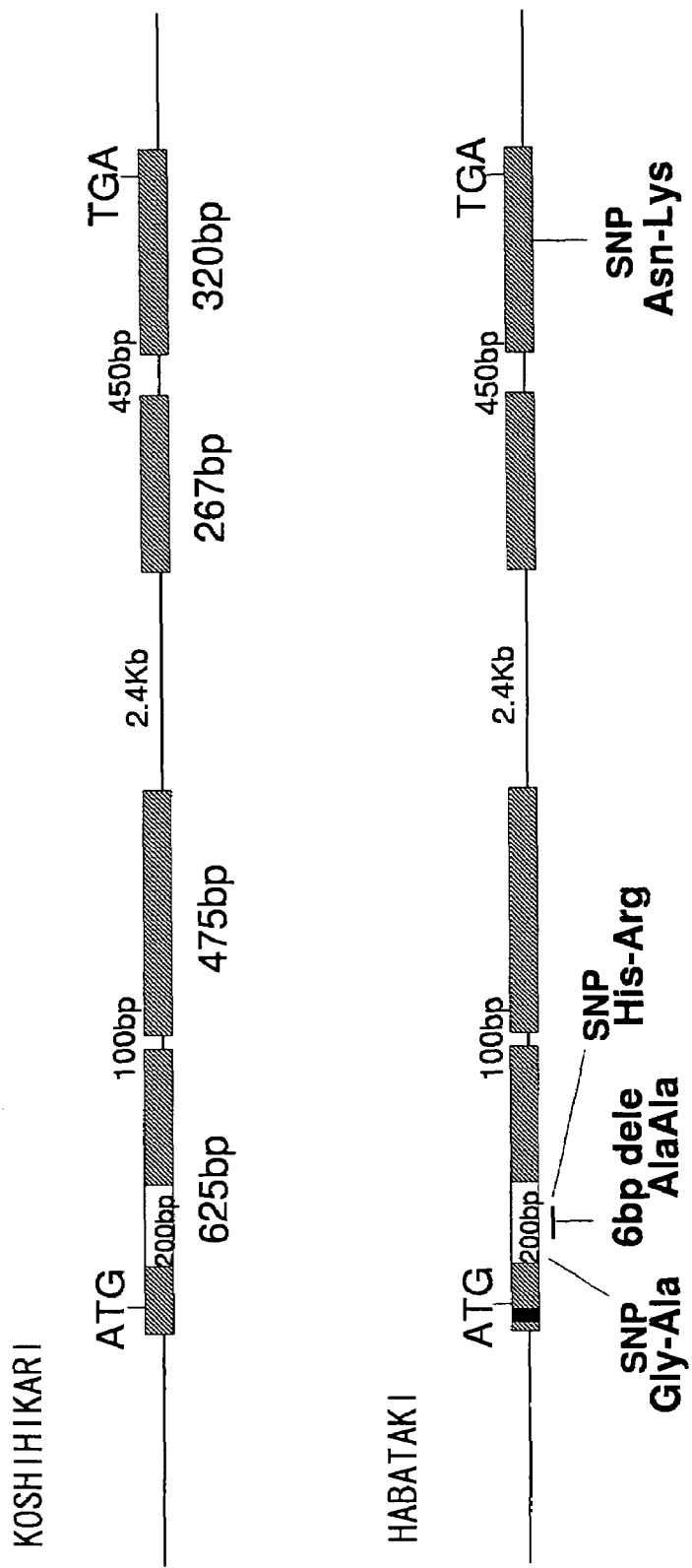
FIG. 5 compares the high-resolution linkage maps of Yielding QTL(YQ) of Koshihikari and Habataki.

The BC3F2 population was used to investigate the phenotype and genotype (F2 and F3) using molecular markers, and linkage analysis was performed again. The results showed that YQ1 is located at the region between molecular markers 6A and 8A (FIG. 3). As a result of performing high-resolution linkage analysis using a segregating population (12500 individuals) of YQ to specify the region of the YQ1 locus, YQ1 was specified to be a region of approximately 8 Kb positioned between molecular markers 4A9 and 20 (FIG. 4). When gene prediction was performed in this region, a single gene was predicted, and as a result of a homology search, a gene that is highly homologous to CKX (cytokinin oxidase) was found (FIG. 4). When the nucleotide sequence of this CKX gene was determined for Habataki and Koshihikari, differences in the nucleotides were found, and the CKX of Habataki seemed to have lost its function (FIG. 5).

EXAMPLE 4

Analysis of CKX Genes in the Rice Genome

Figure 6:
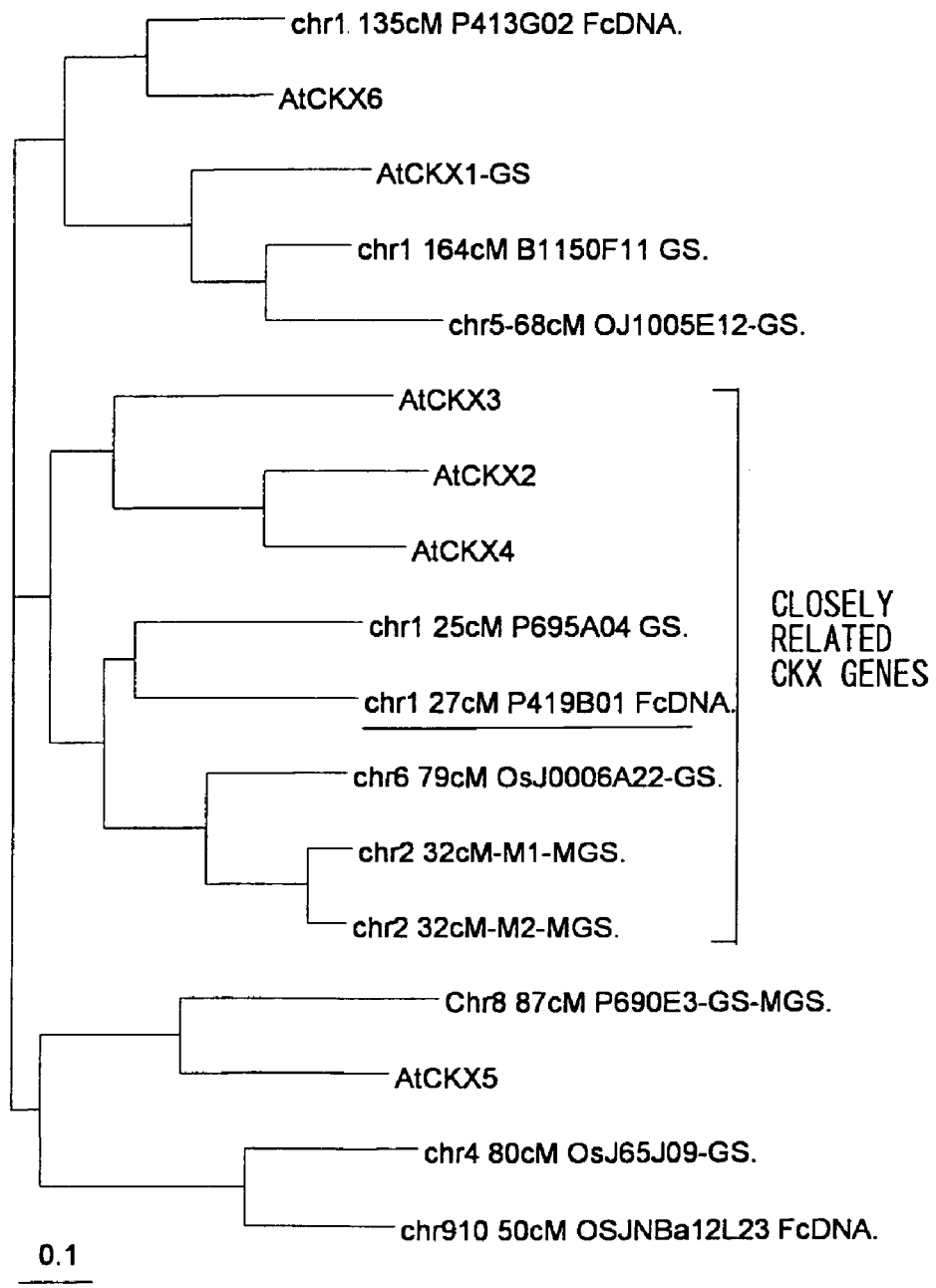
FIG. 6 shows a phylogenetic tree of the CKX genes of *Arabidopsis thaliana* and rice. p FIG. 7 compares the sequences of the CKX genes (SEQ ID NOS: 7-14 respectively, in order of appearance).
Figure 7:
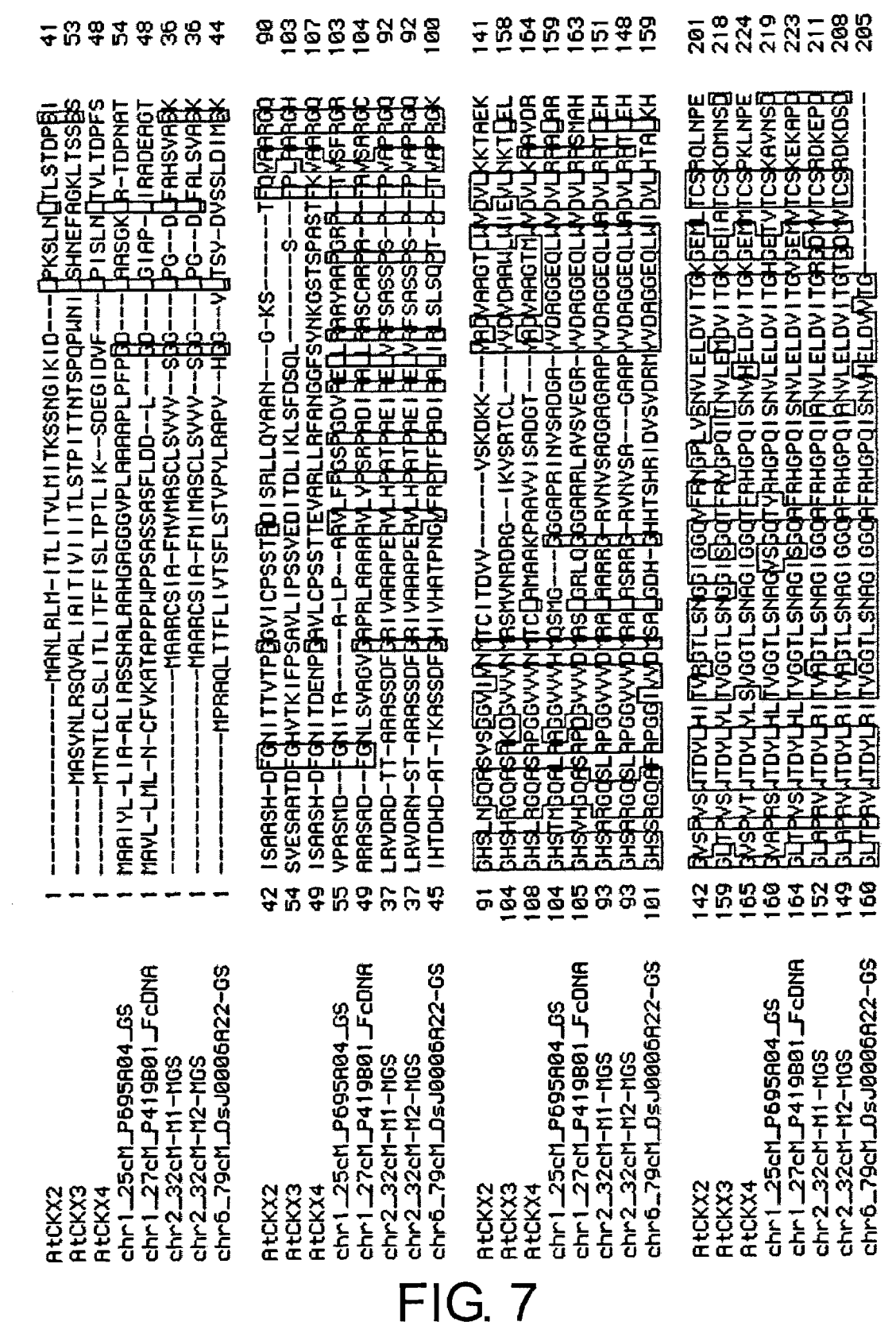
Figure 8:
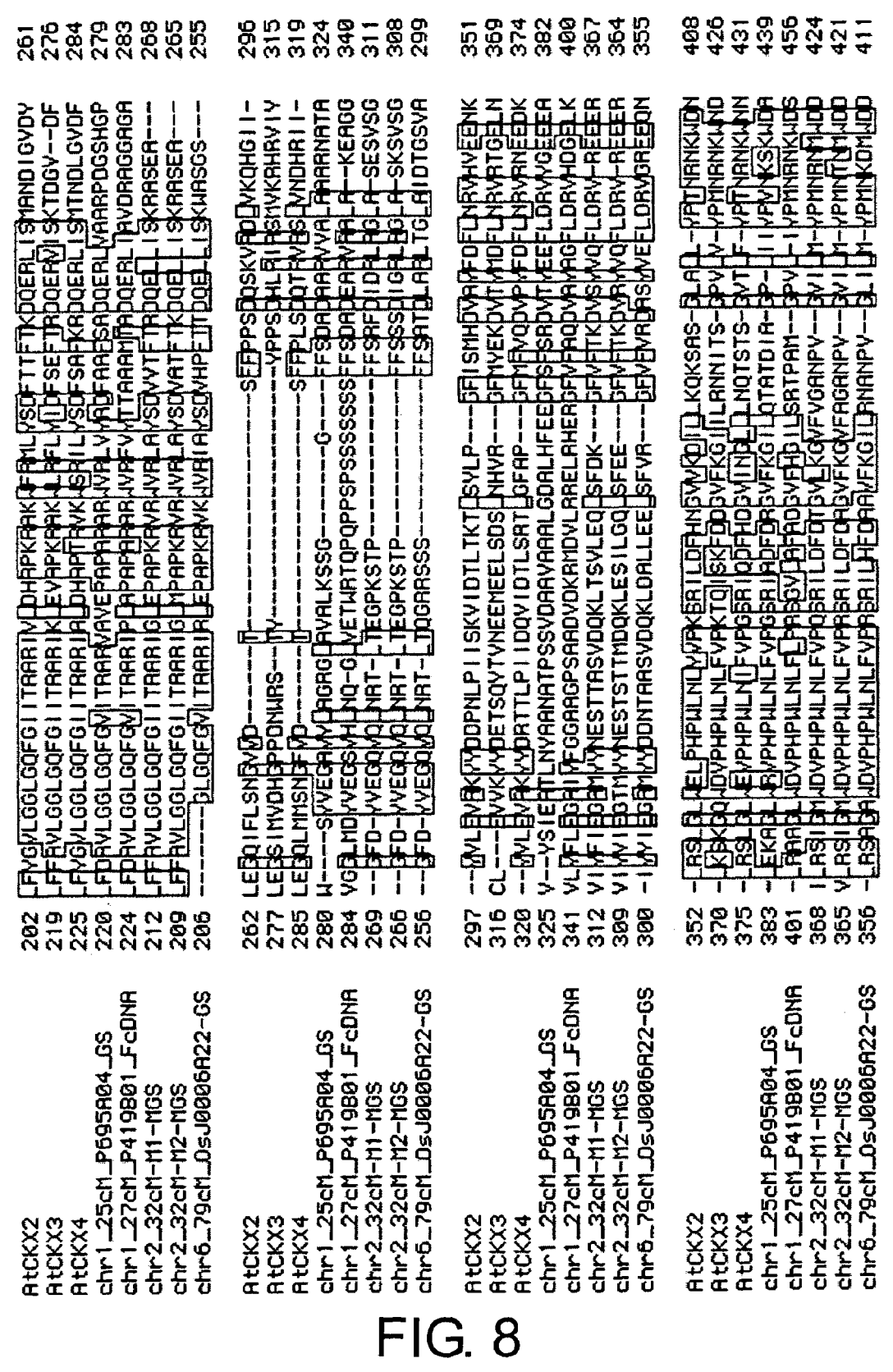
Figure 9:
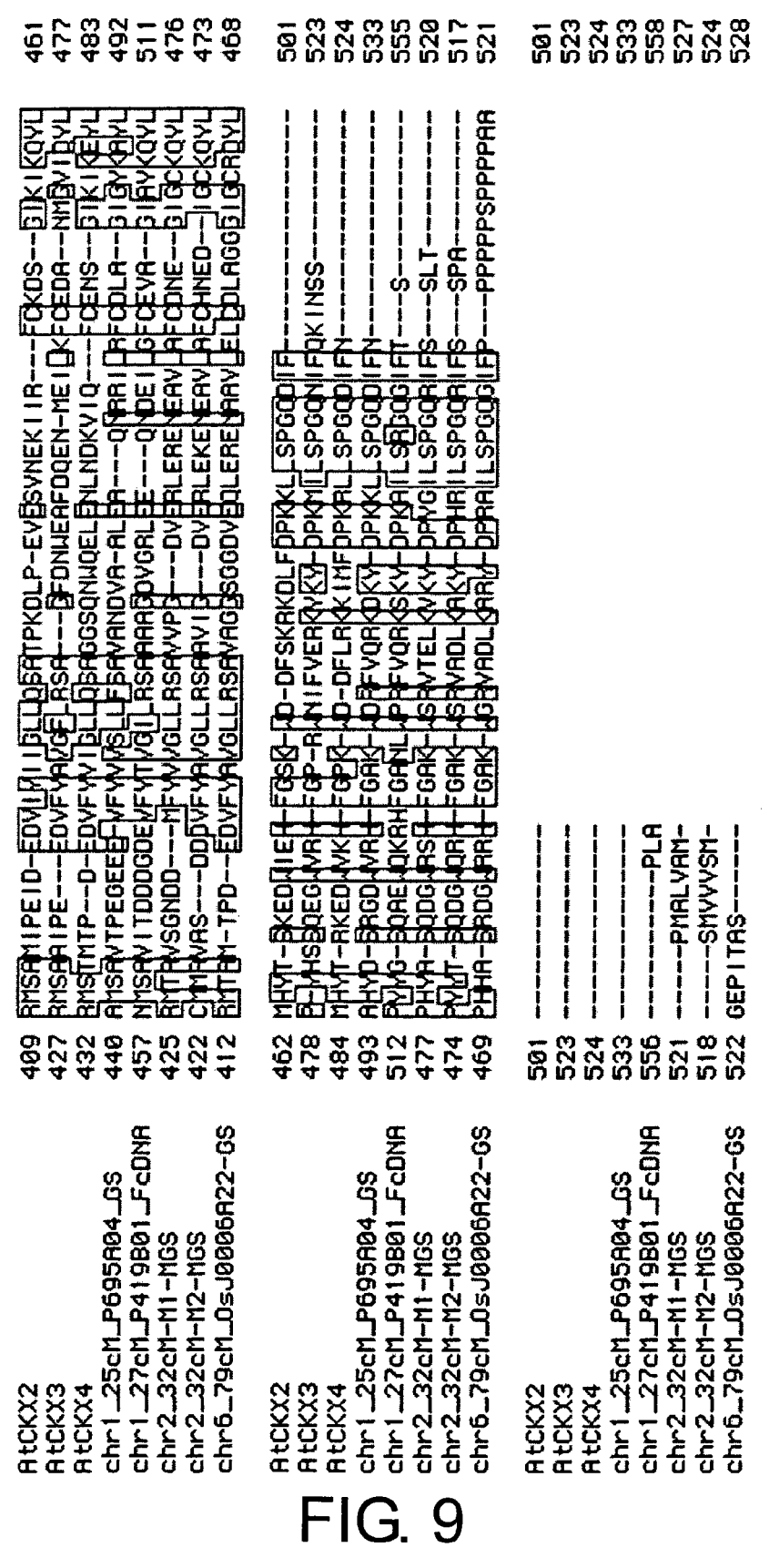
Figure 10:
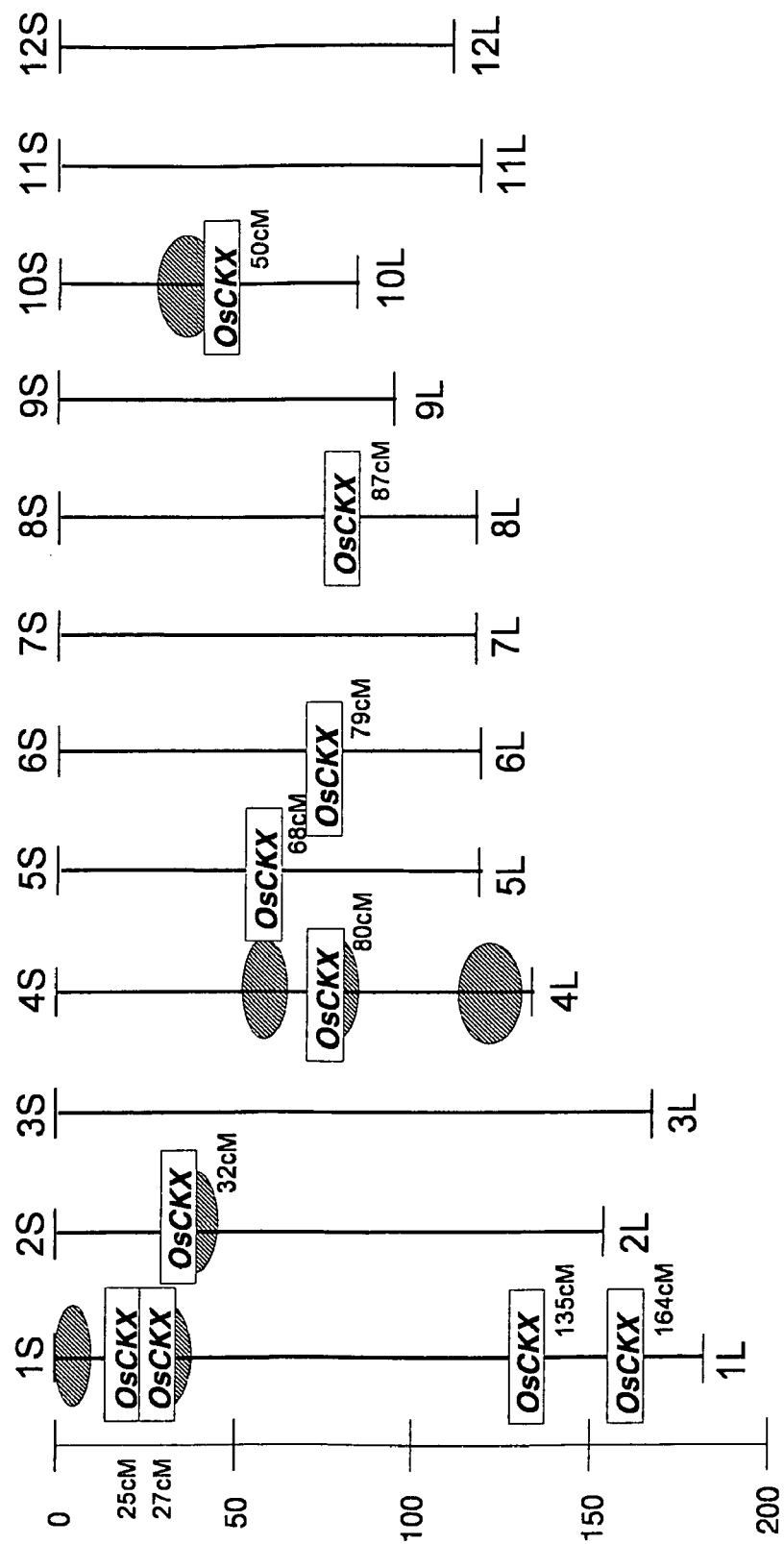
FIG. 10 shows all of the CKX gene loci in rice.

When the rice genomic sequence was searched to analyze the CKX gene in rice, eleven CKX genes were found in the rice genome. When a phylogenic tree was constructed for these genes as well as the CKX genes in *Arabidopsis thaliana*, AtCKX2, 3, and 4 of *Arabidopsis thaliana*, and five rice CKX genes (CKX located on Chr.1 25 cM P695A4, CKX located on Chr.127 P419B01 (the present gene), CKX gene located on Chr.6 79 cM OsJ0006A22-GS, and two CKX genes located on Chr.2 32 cM) were found to be very closely related (FIG. 6). When the homologies of these genes were investigated, they were found to be highly homologous at the amino acid level (FIGS. 7 to 9). Furthermore, when the locus positions of all CKX genes in rice were confirmed, some of them were found to be located on the YQ regions (FIG. 10).

INDUSTRIAL APPLICABILITY

Deletion of the function of the CKX gene provided by the present invention increases the particle-bearing number of plants. Accordingly, regulating the expression of this DNA, using methods such as the antisense method and ribozyme method, can result in increasing the yield of grain. Since genomic synteny (genetic homology) is very highly conserved among grains, application of the rice CKX gene in breeding grains, such as wheat, barley, and corn, can be expected. Furthermore, since the CKX gene is not limited to grains and is widely distributed among plants, deletion of the CKX gene function may increase the number of flowers and seeds (glumous flowers) in all plants, leading to increased yield.

Furthermore, the present invention provides methods of genetic diagnosis for determining the increase or decrease in the particle-bearing number of a plant. Determination of the increase and decrease of the particle-bearing number of plants at the genetic level can be performed more conveniently and reliably compared to determination from the phenotype. Therefore, the method for evaluating the increase and decrease of particle-bearing number of this invention may greatly contribute to the breeding of improved plant varieties.

The invention claimed is:

1. An isolated DNA encoding a protein whose deletion of function causes an increase in the glumous flowers, fruits, or seeds of a plant, wherein the DNA is any one of (a) to (c):
   (a) a DNA encoding a protein comprising the amino acid sequence of SEQ ID NO:3;
   (b) a DNA consisting of the coding region of the nucleotide sequence of SEQ ID NO:1; and
   (c) a DNA consisting of the nucleotide sequence of SEQ ID NO:2.

2. The DNA of claim 1, wherein the DNA is isolated from rice.

3. An isolated DNA encoding an RNA fully complementary to a transcript of the DNA of claim 1.

4. A vector comprising the DNA of any one of claims 1, 2, or 3.

5. A host cell transformed with the vector of claim 4.

6. A plant cell transformed with the vector of claim 4.

7. A transformed plant comprising the plant cell of claim 6.

8. A transformed plant that is an offspring or a clone of the transformed plant of claim 7.

9. A transgenic reproductive material of the transformed plant of claim 7.

10. A method for producing a transformed plant, wherein the method comprises the steps of introducing the DNA of any one of claims 1, 2, or 3 into a plant cell, and regenerating a plant from said plant cell.

11. An agent for increasing the number of glumous flowers, fruits, or seeds of a plant, wherein the agent comprises the DNA of claim 1 as an active ingredient.

* * * * *